United States Patent
Shao et al.

(10) Patent No.: US 10,934,345 B2
(45) Date of Patent: Mar. 2, 2021

(54) BROADLY NEUTRALIZING ANTIBODIES AGAINST HIV-1 AND USE THEREOF

(71) Applicants: NATIONAL CENTER FOR AIDS/STD CONTROL & PREVENTION, CHINESE CENTER FOR DISEASE CONTROL AND PREVENTION, Beijing (CN); THE SCRIPPS RESEARCH INSTITUTE, La Jolla, CA (US)

(72) Inventors: Yiming Shao, Beijing (CN); Jiang Zhu, La Jolla, CA (US); Yuxing Li, La Jolla, CA (US); Ian A. Wilson, La Jolla, CA (US); Leopold Kong, La Jolla, CA (US); Bin Ju, Beijing (CN); Linling He, La Jolla, CA (US); Li Ren, Beijing (CN); Yajing Chen, La Jolla, CA (US); Jiandong Liu, Beijing (CN)

(73) Assignees: NATIONAL CENTER FOR AIDS/STD CONTROL AND PREVENTION, CHINESE CENTER FOR DISEASE CONTROL AND PREVENTION, Beijing (CN); THE SCRIPPS RESEARCH INSTITUTE, La Jolla, CA (US)

( * ) Notice: Subject to any disclaimer, the term of this patent is extended or adjusted under 35 U.S.C. 154(b) by 0 days.

(21) Appl. No.: 16/075,211

(22) PCT Filed: Jan. 26, 2017

(86) PCT No.: PCT/CN2017/072751
§ 371 (c)(1),
(2) Date: Aug. 3, 2018

(87) PCT Pub. No.: WO2017/133640
PCT Pub. Date: Aug. 10, 2017

(65) Prior Publication Data
US 2019/0002539 A1    Jan. 3, 2019

(30) Foreign Application Priority Data
Feb. 3, 2016  (CN) .......................... 201610076092.0

(51) Int. Cl.
| C07K 16/10 | (2006.01) |
| A61P 31/18 | (2006.01) |
| C12N 15/113 | (2010.01) |
| G01N 33/569 | (2006.01) |
| G01N 33/577 | (2006.01) |

(52) U.S. Cl.
CPC .......... *C07K 16/1063* (2013.01); *A61P 31/18* (2018.01); *C12N 15/1131* (2013.01); *G01N 33/569* (2013.01); *G01N 33/577* (2013.01); *C07K 2317/21* (2013.01); *C07K 2317/33* (2013.01); *C07K 2317/51* (2013.01); *C07K 2317/515* (2013.01); *C07K 2317/55* (2013.01); *C07K 2317/76* (2013.01); *C07K 2317/92* (2013.01); *G01N 2333/16* (2013.01)

(58) Field of Classification Search
CPC ............ C07K 16/1063; C07K 2317/56; C07K 2317/565
See application file for complete search history.

(56) References Cited

U.S. PATENT DOCUMENTS

| 7,229,619 B1 | 6/2007 | Young et al. |
| 2013/0209454 A1 | 8/2013 | Diskin et al. |

FOREIGN PATENT DOCUMENTS

| CN | 103403026 A | 11/2013 |
| CN | 104271597 A | 1/2015 |
| EP | 2 975 053 | 1/2016 |
| WO | WO 2011/092593 | 8/2011 |
| WO | WO 2013/142324 | 9/2013 |
| WO | WO 2015/128846 | 9/2015 |

OTHER PUBLICATIONS

Xiang, J., et al., 1999, Light-chain framework region residue Tyr71 of chimeric B72.3 antibody plays an important role in influencing the TAG72 antigen binding, Prot. Engineering 12(5):417-421.*
Winkler, K., et al., 2000, Changing the antigen binding specificity by single point mutations of an anti-p24 (HIV-1) antibody, J. Immunol. 165:4505-4514.*
Sela-Culang, I., et al., Oct. 2013, The structural basis of antibody-antigen recognition, Front. Immunol. 4 Article 302:1-13.*
Liu, Z., et al., 1999, Fine mapping of the antigen-antibody interaction of scFv215, a recombinant antibody inhibiting RNA polymerase II from *Drosophila melanogaster*, J. Mol. Recognition 12:103-111.*
Wu, X., et al., Sep. 2011, Focused evolution of HIV-1 neutralizing antibodies revealed by structures and deep sequencing, Science 333(6049):1593-1602.*
European Search Report corresponding to European Application No. 17746960.8-1116/3414266 dated May 17, 2019.
Xueling Wu et al. (2010) Rational design of envelope identifies broadly neutralizing human monoclonal antibodies to HIV-1, Science, AAAS, American Assoc. for the Advancement of Science 329(5993):856-861.
Burton et al. (1994) Efficient neutralization of primary isolates of HIV-1 by a recombinant human monoclonal antibody. Science 266:1024-1027.
Chothia et al. (1987) Canonical structures for the hypervariable regions of immunoglobulins. J. Mol. Biol. 196:901-917.
Huang et al. (2012) Broad and potent neutralization of HIV-1 by a gp41-specific human antibody. Nature 491:406-412.

(Continued)

*Primary Examiner* — Jeffrey S Parkin
(74) *Attorney, Agent, or Firm* — Jenkins, Wilson, Taylor & Hunt, P.A.

(57) ABSTRACT

Broadly neutralizing antibodies against HIV-1 which specifically bind to gp120 of HIV-1, a method of preparing such antibodies and the use thereof are provided.

19 Claims, 9 Drawing Sheets

Specification includes a Sequence Listing.

(56) References Cited

OTHER PUBLICATIONS

Huang et al. Broad and potent HIV-1 neutralization by a human antibody that binds the gp41-120 interface. Nature 515:138-142.
International Search Report corresponding to International Patent Application No. PCT/CN2017/072751 dated May 8, 2017.
Julien et al. (2013) Broadly Neutralizing Antibody PGT121 Allosterically Modulates CD4 Binding via Recognition of the HIV-1 gp120 V3 Base and Multiple Surrounding Glycans. PLoS Pathogens 9(5):1553-7374.
Kong et al. (2016) Key gp120 Glycans Pose Roadblocks to the Rapid Development of VRC01-Class Antibodies in an HIV-1-Infected Chinese Donor. Immunity 44(4):930-950.
Li et al. (2005) Human Immunodeficiency Virus Type 1 env Clones from Acute and Early Subtype B Infections for Standardized Assessments of Vaccine-Elicited Neutralizing Antibodies. J. Virol. 79:10108-10125.
McLellan et al. (2011) Structure of HIV-1 gp120 V1/V2 domain with broadly neutralizing antibody PG9. Nature 480:336-343.
Wu et al. (2010) Rational design of envelope identifies broadly neutralizing human monoclonal antibodies to HIV-1. Science 329:856-861.

* cited by examiner

Heavy chain

```
                 -------FR1-------              -----CDR1------    ---FR2---              CDR2
IgHV1-02*02      QVQLVQSGAEVKKPGASVKVSCKASGYTFTGYYMHWVRQAPGQGLEWMGWINPNSGGTNYAQKFQG
DRVIA7           QVQLVESGTQFRRPGASVRLSCEASGYTFISSFIHWIRQGPGQGLEWMGWMNPRHGAVNYPRRFQG

IgHD1-7*01   IgHJ5*02
                 ----------FR3----------              CDR3              ---FR4---
IgHV1-02*02      RVTMTRDTSISTAYMELSRLRSDDTAVYYCAR
DRVIA7           KVTMTRDTSIDTAYMELRDLRSDDTAMYFCVTSRTKDYDWDFVWGQGTLVVVSS
```

FIG. 1A

Heavy chain

```
                 -------FR1--------        ----CDR1----  ---FR2--        CDR2
IgHV1-02*02   QVQLVQSGAEVKKPGASVKVSCKASGYTFTGYYMHWVRQAPGQGLEWMGWINPSGGTNYAQKFQG
VRC01         QVQLVQSGGQMKKPGESMRISCSASGYEFIDCTLNWIRLAPGKRPEWMGWLKPRGGAVNYARPLQG

IgHD3-16*02   IgHJ1*01
                 ----------FR3---------          CDR3         ----FR4----
IgHV1-02*02   RVTMTRDTSISTAYMELSRLRSDDTAVYYCAR
VRC01         RVTMTRDVVSDTAFLELRSLTVDDTAVYFCTRGKNCDYNWDFEHWGRGTPVIVSS
```

FIG. 1B

Light chain

```
                 -------FR1-----------     -----CDR1-------    --------FR2------  ---CDR2---
IgKV1-5*03       DIQMTQSPSTLSASVGDRVTITCRASQSISSWLAWYQQKPGKAPKLLIYKASSLES
DRVIA7           DIQMTQSPVTLSASIGDRVTITCRASQRIDNWVAWYQQKPGRAPKLLIYKASILET

IgKJ1*01
                 --------------FR3-----------    -----CDR3-----   ---FR4----
IgKV1-5*03       GVPSRFSGSGSGTEFTLTITSSLQPSSFATYYCQQ               FGRGTKIDIK
DRVIA7           GVPSRFSGSGSGTEFTLSINSLQPDDVATYYCQQFEE             FGRGTKIDIK
```

FIG. 1C

Light chain

```
             -------FR1----------   ----CDR1----              ------FR2------  ____CDR2____
IgKV3-11*01  EIVLTQSPATLSLSPGERATLSCRASQSVSSYLAWYQQKPGQAPRLLIYDASNRAT
VRC01        EIVLTQSPGTLSLSPGETAIISCRTSQYGS     LAWYQQRPGQAPRLVIYSGSTRAA

----------FR3----------                     ___CDR3___           ----FR4----
                                                    IgKJ2*01
IgKV3-11*01  GIPARFSGSGSGTDFTLTISSLEPEDFAVYYCQQ
VRC01        GIPDRFSGSRWGPDYNLTISNLESGDFGVYYCQQYEF                             FGQGTKVQVDIK
```

FIG. 1D

SEQUENCE LISTING

```
<160> NUMBER OF SEQ ID NOS: 15

<210> SEQ ID NO 1
<211> LENGTH: 360
<212> TYPE: DNA
<213> ORGANISM: Homo sapiens

<400> SEQUENCE: 1
caggtgcagc tggtggagtc tgggactcaa tttaggaggc ctgggcctc  agtgagactc      60 tcctgcgagg cttctggata caccttcatc tcctccttta tacattggat aaggcagggc     120
cctggccaag ggcttgagtg gatggggtgg atgaaccta gacatgcgc  cgttaattac     180 ccgcggaggt ttcagggtaa ggtgaccatg accagggaca cgtccatcga cacagcctac    240
atggagctgc gtgacctgag atctgacgac acggccatgt atttctgtgt gacatctcgg    300
actaaagact atgactggga ctttgtctgg ggccagggga ccctggtcgt cgtctcctca    360

<210> SEQ ID NO 2
<211> LENGTH: 120
<212> TYPE: PRT
<213> ORGANISM: Homo sapiens

<400> SEQUENCE: 2

Gln Val Gln Leu Val Glu Ser Gly Thr Gln Phe Arg Arg Pro Gly Ala
1               5                   10                  15

Ser Val Arg Leu Ser Cys Glu Ala Ser Gly Tyr Thr Phe Ile Ser Ser
            20                  25                  30
```

```
Phe Ile His Trp Ile Arg Gln Gly Pro Gly Gln Gly Leu Glu Trp Met
            35                  40                  45
Gly Trp Met Asn Pro Arg His Gly Ala Val Asn Tyr Pro Arg Arg Phe
 50                      55                  60
Gln Gly Lys Val Thr Met Thr Arg Asp Thr Ser Ile Asp Thr Ala Tyr
 65                  70                  75                  80
Met Glu Leu Arg Asp Leu Arg Ser Asp Thr Ala Met Tyr Phe Cys
                 85                  90                  95
Val Thr Ser Arg Thr Lys Asp Tyr Asp Trp Asp Phe Val Trp Gly Gln
                100                 105                 110
Gly Thr Leu Val Val Val Ser Ser
            115                 120

<210> SEQ ID NO 3
<211> LENGTH: 360
<212> TYPE: DNA
<213> ORGANISM: Homo sapiens

<400> SEQUENCE: 3
cagaaacaac tggtgcagtc tgggactcaa tttaagaggc ctggggcctc agtgagactc        60
tcctgcgagg cttctggata caccttcatc tcctccttca tacattggat aaggcagggc       120
cctggccaag gacttgagtg gatggggtgg atgaatccta gacatggcgg cgtaaattac       180
cctcggaggt ttcagggtaa ggtcaccatg accaggacac gtccatcga cacagcctac        240 atggagctgc gtgacctgag atctgacgac acggccatgt atttctgtgt gacctcccgg       300
actaaagact atgactggga ctttgtctgg ggccagggga ccctggtcgt cgtctcctca       360

<210> SEQ ID NO 4
<211> LENGTH: 120
<212> TYPE: PRT
<213> ORGANISM: Homo sapiens

<400> SEQUENCE: 4

Gln Lys Gln Leu Val Gln Ser Gly Thr Gln Phe Lys Arg Pro Gly Ala
 1               5                  10                  15
Ser Val Arg Leu Ser Cys Glu Ala Ser Gly Tyr Thr Phe Ile Ser Ser
             20                  25                  30
Phe Ile His Trp Ile Arg Gln Gly Pro Gly Gln Gly Leu Glu Trp Met
            35                  40                  45
Gly Trp Met Asn Pro Arg His Gly Gly Val Asn Tyr Pro Arg Arg Phe
 50                      55                  60
Gln Gly Lys Val Thr Met Thr Arg Asp Thr Ser Ile Asp Thr Ala Tyr
 65                  70                  75                  80
Met Glu Leu Arg Asp Leu Arg Ser Asp Asp Thr Ala Met Tyr Phe Cys
                 85                  90                  95
Val Thr Ser Arg Thr Lys Asp Tyr Asp Trp Asp Phe Val Trp Gly Gln
                100                 105                 110
Gly Thr Leu Val Val Val Ser Ser
            115                 120

<210> SEQ ID NO 5
<211> LENGTH: 360
<212> TYPE: DNA
<213> ORGANISM: Homo sapiens

<400> SEQUENCE: 5
cagagacaac tggtgcagtc tgggactcag tttaagaggc ctggggcctc agtgagactc        60
```

```
tcctgcgagg cttctggata caccttcatc tcatcctta tacactggat acgacaggcc    120
cctggccaag gccttgagtg gatggggtgg atgaaccta gacatggcgc cgtgaattac    180
cctcggaggt ttcagggtaa ggtcaccatg tccagggaca cgtctatcga cacagcctac    240
atggagctgc gtgacctgag agctgacgac acggccactt atttctgtgt gacctcccgg    300
actaatgact atgactggga ctttgtctgg ggccagggga ccctggtcgt cgtctcctca    360
```

<210> SEQ ID NO 6
<211> LENGTH: 120
<212> TYPE: PRT
<213> ORGANISM: Homo sapiens

<400> SEQUENCE: 6

Gln Arg Gln Leu Val Gln Ser Gly Thr Gln Phe Lys Arg Pro Gly Ala
1               5                   10                  15

Ser Val Arg Leu Ser Cys Glu Ala Ser Gly Tyr Thr Phe Ile Ser Ser
            20                  25                  30

Phe Ile His Trp Ile Arg Gln Ala Pro Gly Gln Gly Leu Glu Trp Met
        35                  40                  45

Gly Trp Met Asn Pro Arg His Gly Ala Val Asn Tyr Pro Arg Arg Phe
    50                  55                  60

Gln Gly Lys Val Thr Met Ser Arg Asp Thr Ser Ile Asp Thr Ala Tyr
65                  70                  75                  80

Met Glu Leu Arg Asp Leu Arg Ala Asp Asp Thr Ala Thr Tyr Phe Cys
                85                  90                  95

Val Thr Ser Arg Thr Asn Asp Tyr Asp Trp Asp Phe Val Trp Gly Gln
            100                 105                 110

Gly Thr Leu Val Val Val Ser Ser
        115                 120

<210> SEQ ID NO 7
<211> LENGTH: 309
<212> TYPE: DNA
<213> ORGANISM: Homo sapiens

<400> SEQUENCE: 7

```
gacatccaga tgacccagtc tccagtcacc ctgtctgcgt ctataggaga cagagtcacc    60
atcacttgtc gggccagtca gaggatagat aactgggtgg cctggtatca gcagaaacca    120
gggagagccc ctaaactcct catctataag gcctctattt tagagacagg ggtcccatct    180
cgattcagcg gcagtgggtc tgggacagaa ttcactctct ccatcaacag cctgcagcct    240
gatgatgtcg caacttatta ctgccaacaa tttgaggagt tcggccgagg gaccaagatt    300
gacatcaaa                                                           309
```

<210> SEQ ID NO 8
<211> LENGTH: 103
<212> TYPE: PRT
<213> ORGANISM: Homo sapiens

<400> SEQUENCE: 8

Asp Ile Gln Met Thr Gln Ser Pro Val Thr Leu Ser Ala Ser Ile Gly
1               5                   10                  15

Asp Arg Val Thr Ile Thr Cys Arg Ala Ser Gln Arg Ile Asp Asn Trp
            20                  25                  30

Val Ala Trp Tyr Gln Gln Lys Pro Gly Arg Ala Pro Lys Leu Leu Ile
        35                  40                  45

Tyr Lys Ala Ser Ile Leu Glu Thr Gly Val Pro Ser Arg Phe Ser Gly
            50                  55                  60

Ser Gly Ser Gly Thr Glu Phe Thr Leu Ser Ile Asn Ser Leu Gln Pro
 65                  70                  75                  80

Asp Asp Val Ala Thr Tyr Tyr Cys Gln Gln Phe Glu Glu Phe Gly Arg
                 85                  90                  95

Gly Thr Lys Ile Asp Ile Lys
            100

<210> SEQ ID NO 9
<211> LENGTH: 315
<212> TYPE: DNA
<213> ORGANISM: Homo sapiens

<400> SEQUENCE: 9
gaaattgtgt tgacacagtc tccaggcacc ctgtctttgt ctccagggga aacagccatc      60
atctcttgtc ggaccagtca gtatggttcc ttagcctggt atcaacagag gcccggccag     120
gcccccaggc tcgtcatcta ttcgggctct actcgggccg ctggcatccc agacaggttc     180
agcggcagtc ggtgggggcc agactacaat ctcaccatca gcaacctgga gtcgggagat     240
tttggtgttt attattgcca gcagtatgaa ttttttggcc aggggaccaa ggtccaggtc     300
gacattaaac gtacg                                                      315

<210> SEQ ID NO 10
<211> LENGTH: 105
<212> TYPE: PRT
<213> ORGANISM: Homo sapiens

<400> SEQUENCE: 10

Glu Ile Val Leu Thr Gln Ser Pro Gly Thr Leu Ser Leu Ser Pro Gly
 1               5                  10                  15

Glu Thr Ala Ile Ile Ser Cys Arg Thr Ser Gln Tyr Gly Ser Leu Ala
             20                  25                  30

Trp Tyr Gln Gln Arg Pro Gly Gln Ala Pro Arg Leu Val Ile Tyr Ser
         35                  40                  45

Gly Ser Thr Arg Ala Ala Gly Ile Pro Asp Arg Phe Ser Gly Ser Arg
     50                  55                  60

Trp Gly Pro Asp Tyr Asn Leu Thr Ile Ser Asn Leu Glu Ser Gly Asp
 65                  70                  75                  80

Phe Gly Val Tyr Tyr Cys Gln Gln Tyr Glu Phe Phe Gly Gln Gly Thr
                 85                  90                  95

Lys Val Gln Val Asp Ile Lys Arg Thr
            100                 105

<210> SEQ ID NO 11
<211> LENGTH: 98
<212> TYPE: PRT
<213> ORGANISM: Homo sapiens

<400> SEQUENCE: 11

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Gly Tyr
             20                  25                  30

Tyr Met His Trp Val Arg Gln Ala Pro Gly Gln Gly Leu Glu Trp Met
         35                  40                  45

-continued

Gly Trp Ile Asn Pro Asn Ser Gly Gly Thr Asn Tyr Ala Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 12
<211> LENGTH: 121
<212> TYPE: PRT
<213> ORGANISM: Homo sapiens

<400> SEQUENCE: 12

Gln Val Gln Leu Val Gln Ser Gly Gly Gln Met Lys Lys Pro Gly Glu
1               5                   10                  15

Ser Met Arg Ile Ser Cys Ser Ala Ser Gly Tyr Glu Phe Ile Asp Cys
                20                  25                  30

Thr Leu Asn Trp Ile Arg Leu Ala Pro Gly Lys Arg Pro Glu Trp Met
            35                  40                  45

Gly Trp Leu Lys Pro Arg Gly Gly Ala Val Asn Tyr Ala Arg Pro Leu
        50                  55                  60

Gln Gly Arg Val Thr Met Thr Arg Asp Val Tyr Ser Asp Thr Ala Phe
65                  70                  75                  80

Leu Glu Leu Arg Ser Leu Thr Val Asp Asp Thr Ala Val Tyr Phe Cys
                85                  90                  95

Thr Arg Gly Lys Asn Cys Asp Tyr Asn Trp Asp Phe Glu His Trp Gly
            100                 105                 110

Arg Gly Thr Pro Val Ile Val Ser Ser
        115                 120

<210> SEQ ID NO 13
<211> LENGTH: 90
<212> TYPE: PRT
<213> ORGANISM: Homo sapiens

<400> SEQUENCE: 13

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Lys Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Ser Ser Phe Ala Thr Tyr Tyr Cys Gln Gln
                85                  90

<210> SEQ ID NO 14
<211> LENGTH: 90
<212> TYPE: PRT
<213> ORGANISM: Homo sapiens

<400> SEQUENCE: 14

Glu Ile Val Leu Thr Gln Ser Pro Ala Thr Leu Ser Leu Ser Pro Gly
1               5                   10                  15

```
Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln
                85                  90

<210> SEQ ID NO 15
<211> LENGTH: 103
<212> TYPE: PRT
<213> ORGANISM: Homo sapiens

<400> SEQUENCE: 15

Glu Ile Val Leu Thr Gln Ser Pro Gly Thr Leu Ser Leu Ser Pro Gly
1               5                   10                  15

Glu Thr Ala Ile Ile Ser Cys Arg Thr Ser Gln Tyr Gly Ser Leu Ala
            20                  25                  30

Trp Tyr Gln Gln Arg Pro Gly Gln Ala Pro Arg Leu Val Ile Tyr Ser
        35                  40                  45

Gly Ser Thr Arg Ala Ala Gly Ile Pro Asp Arg Phe Ser Gly Ser Arg
    50                  55                  60

Trp Gly Pro Asp Tyr Asn Leu Thr Ile Ser Asn Leu Glu Ser Gly Asp
65                  70                  75                  80

Phe Gly Val Tyr Tyr Cys Gln Gln Tyr Glu Phe Phe Gly Gln Gly Thr
                85                  90                  95

Lys Val Gln Val Asp Ile Lys
                100
```

BROADLY NEUTRALIZING ANTIBODIES AGAINST HIV-1 AND USE THEREOF

TECHNICAL FIELD

The present invention relates to broadly neutralizing antibodies against HIV-1 which specifically bind to gp120 of HIV-1. The present invention also relates to the methods for preparing such antibodies and the use thereof.

TECHNICAL BACKGROUND

HIV-1 neutralizing antibodies (NAbs) could effectively block HIV-1 entry into human CD4+T cells. As a therapeutic strategy, potent and broadly reactive NAbs have been developed in AIDS research.

Monoclonal antibody b12 was isolated from a phage display library, which neutralizes about 40% known HIV-1 isolates[1]. With the improvement of techniques including single B cell sorting and deep sequencing, a number of monoclonal broadly neutralizing antibodies have been isolated from HIV-1-infected donors which recognize a range of epitopes on HIV-1 viral spike since 2010. These sites include the CD4-binding site on gp120 (VRC01)[2], the glycan-containing regions of V1V2 on gp120 (PG9 and PG16)[3], the V3 region centered on the N332 glycan of gp120 (PGT121)[4] and the membrane-proximal external region (MPER) on gp41 (10E8)[5], and a conserved face on contiguous areas of gp41 and gp120 (35022)[6].

Because HIV-1 has various clades and there are different major epidemic strains worldwide, combination of different broadly NAbs will be a more potential treatment strategy for AIDS. Therefore, it is still necessary to develop new potent NAbs for HIV-1.

SUMMARY OF INVENTION

The present invention provides human monoclonal antibodies and functional fragments thereof which are capable of specifically binding to gp120 of HIV-1 and blocking the entry of HIV-1 into target cells. The present invention also provides nucleic acid molecules encoding the above described antibodies or antibody fragments as well as an expression vector comprising at least one nucleic acid molecule as described above. The present invention also provides a host cell transformed with at least one nucleic acid molecule or expression vector as described above. The present invention also provides a method of producing an antibody by using at least one nucleic acid molecule or expression vector or host cell as described above. The present invention also provides a pharmaceutical composition comprising at least one antibody or antibody fragment as described above. In some embodiments, the heavy chain variable domain (VH) of the antibody of the invention comprises (i) VHCDR1, VHCDR2, and VHCDR3 respectively corresponding to amino acids 31-35, 50-66, and 99-109 of SEQ ID NO:2, or (ii) VHCDR1, VHCDR2, and VHCDR3 respectively corresponding to amino acids 31-35, 50-66, and 99-109 of SEQ ID NO:4, or (iii) VHCDR1, VHCDR2, and VHCDR3 respectively corresponding to amino acids 31-35, 50-66, and 99-109 of SEQ ID NO:6, the light chain variable domain (VL) of the antibody of the invention comprises VLCDR1, VLCDR2, and VLCDR3 respectively corresponding to amino acids 24-32, 48-54, and 87-91 of SEQ ID NO:10. The antibodies of the invention are broadly neutralizing antibodies which specifically bind to gp120 of HIV-1.

The present invention also provides method of detecting an HIV-1 infection in a human subject comprising contacting a biological sample from the subject with an antibody or antibody fragment of the present invention, and determining the presence of an immune complex formed by the antibody or the antibody fragment in said sample, wherein the presence of said immune complex indicates that the subject has an HIV-1 infection. In some embodiments, prior to the contacting, the sample is immobilized on a solid substrate. In some other embodiments, prior to the contacting, the antibody or antibody fragment is immobilized on a solid substrate. In some embodiments, the antibody or antibody fragment is labeled with a fluorescent, enzymatic, or radioactive label. In some embodiments, the immune complex is detected by using a second antibody capable of specifically binding to the antibody or antibody fragment. In some other embodiments, the immune complex is detected by using a second antibody capable of specifically binding to an antigen of HIV-1. The present invention also provides a kit for detecting an HIV-1 infection in a human subject, comprising an antibody or antibody fragment of the present invention.

The present invention further provides a method of preventing or treating an HIV-1 infection in a human subject, comprising administering to the subject an effective amount of an antibody or antibody fragment of the invention or a pharmaceutical composition of the invention. In some embodiments, the subject has acquired immune deficiency syndrome (AIDS). In some embodiments, the method further comprises administering to the subject an anti-viral agent against HIV-1.

The present invention also relates to use of the antibody or antibody fragment of the invention in manufacture of a kit for detecting an HIV-1 infection in a human subject or in manufacture of a pharmaceutical composition for preventing or treating an HIV-1 infection in a human subject.

BRIEF DESCRIPTION OF THE DRAWINGS

FIGS. 1A-1B show the sequence analysis of antibody DRVIA7 and antibody VRC01 heavy and light chains with alignment to respective germline genes. In FIG. 1A. the amino acid sequence of the heavy chain of the germline gene IgHV1-02*02 corresponds to SEQ ID NO:11 and the amino acid sequence of the heavy chain of antibody DRVIA7 corresponds to SEQ ID NO:2. In FIG. 1B, the amino acid sequence of the heavy chain of the germline gene IgHV1-02*02 corresponds to SEQ ID NO:11 and the amino acid sequence of the heavy chain of antibody VRC01 corresponds to SEQ ID NO:12. In FIG. 1C, the amino acid sequence of the light chain of the germline gene IgKV1-05*03 corresponds to SEQ ID NO:13 and the amino acid sequence of the light chain of antibody DRVIA7 corresponds to SEQ ID NO:8. In FIG. 1D, the amino acid sequence of the light chain of the germline gene IgKV3-11*01 corresponds to SEQ ID NO:14 and the amino acid sequence of the light chain of antibody VRC01 corresponds to SEQ ID NO:15.

SEQUENCE LISTING

Figure 2:
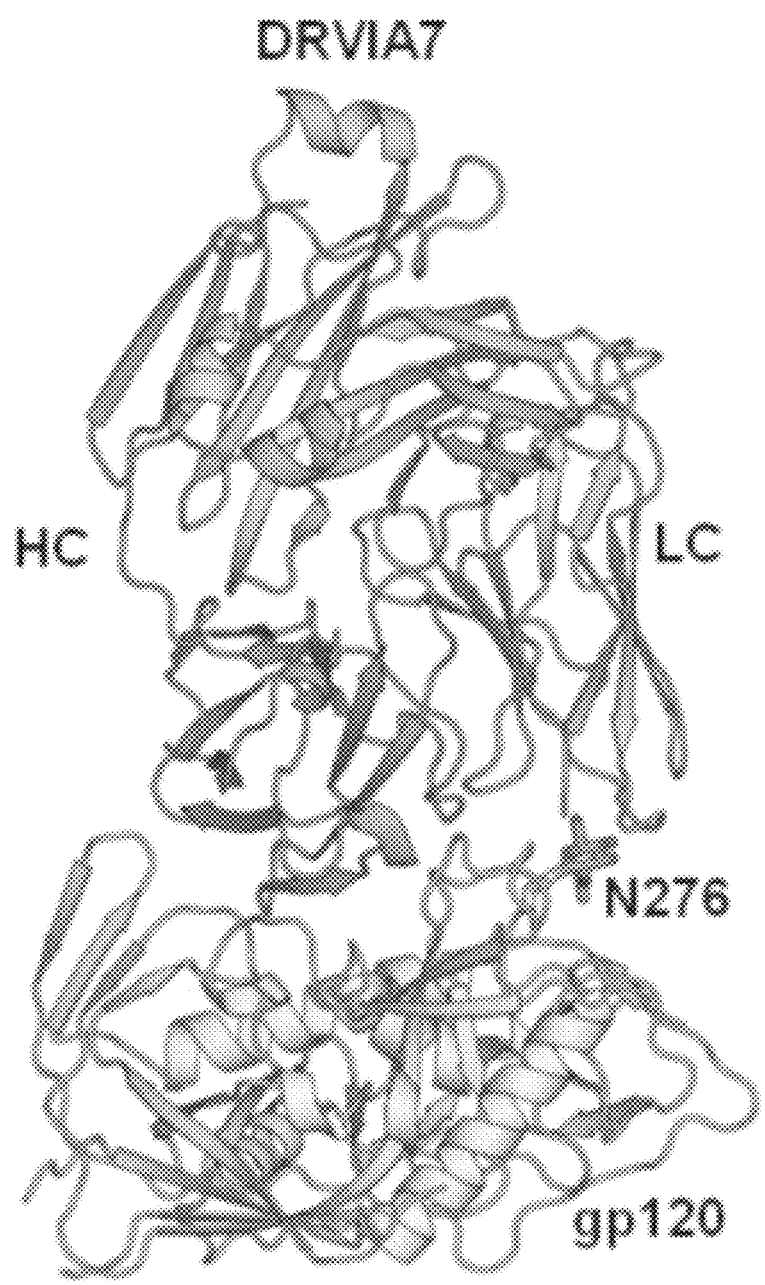
FIG. 2 shows ribbon diagrams of the crystal structure of DRVIA7 bound to gp120.

SEQ ID NO:1 is the sequence encoding the DRVIA7 VH.
SEQ ID NO:2 is the amino acid sequence of the DRVIA7 VH.
SEQ ID NO:3 is the sequence encoding the VH gDRVI01-H1.
SEQ ID NO:4 is the amino acid sequence of the VH gDRVI01-H1.
SEQ ID NO:5 is the sequence encoding the VH gDRVI01-H2.
SEQ ID NO:6 is the amino acid sequence of the VH gDRVI01-H2.
SEQ ID NO:7 is the sequence encoding the DRVIA7 VL.
SEQ ID NO:8 is the amino acid sequence of the DRVIA7 VL.
SEQ ID NO:9 is the sequence encoding the VRC01 VL.
SEQ ID NO:10 is the amino acid sequence of the VRC01 VL.
SEQ ID NO:11 is the amino acid sequence of the heavy chain of germline gene IgHV1-02*02.
SEQ ID NO:12 is the amino acid sequence of the light chain of antibody VRC01.
SEQ ID NO:13 is the amino acid sequence of the light chain of germline gene IgKV1-05*03.
SEQ ID NO:14 is the amino acid sequence of the light chain of germline gene IgKV3-11*01.
SEQ ID NO:15 is the amino acid sequence of the light chain of antibody VRC01 as is the same as SEQ ID NO:10 but lacking the two (2) C-terminal amino acids of SEQ ID NO: 10.

DEPOSITS OF BIOLOGICAL MATERIALS

*Escherichia coli* strain carrying the expression vector containing the heavy chain gene of DRVIA7 was deposited at CGMCC on Dec. 14, 2015 under the Deposit Number CGMCC No. 11879.

*Escherichia coli* strain carrying the expression vector containing the light chain gene of DRVIA7 was deposited at CGMCC on Dec. 14, 2015 under the Deposit Number CGMCC No. 11880.

*Escherichia coli* strain carrying the expression vector containing the heavy chain gene encoding the heavy chain variable domain gDRVI01-H1 was deposited at CGMCC on Dec. 14, 2015 under the Deposit Number CGMCC No. 11883.

*Escherichia coli* strain carrying the expression vector containing the heavy chain gene encoding the heavy chain variable domain gDRVI01-H2 was deposited at CGMCC on Dec. 14, 2015 under the Deposit Number CGMCC No. 11884.

DETAILED DESCRIPTION

Definitions

Unless defined otherwise, all technical and scientific terms used herein have the same meaning as is commonly understood by one of skill in the art to which the invention(s) belong. In addition, the terms and experimental procedures relating to protein and nucleic acid chemistry, molecular biology, cell and tissue culture, microbiology and immunology are those terms and common procedures widely used in the art. Meanwhile, for better understanding of the invention, definitions and explanations of relevant terms are provided below.

As used herein, "antibody" refers to immunoglobulins and immunoglobulin fragments, whether natural or partially or wholly synthetically, such as recombinantly, produced, including any fragment thereof containing at least a portion of the variable region of the immunoglobulin molecule that retains the binding specificity ability of the full-length immunoglobulin. Hence, an antibody includes any protein having a binding domain that is homologous or substantially homologous to an immunoglobulin antigen-binding domain (antibody combining site). Antibodies include antibody fragments, such as anti-HIV-1 antibody fragments. As used herein, the term antibody, thus, includes synthetic antibodies, recombinantly produced antibodies, multispecific antibodies (e.g., bispecific antibodies), human antibodies, non-human antibodies, humanized antibodies, chimeric antibodies, intrabodies, and antibody fragments, such as, but not limited to, Fab fragments, Fab' fragments, F(ab')$_2$ fragments, Fv fragments, disulfide-linked Fvs (dsFv), Fd fragments, Fd' fragments, single-chain Fvs (scFv), single-chain Fabs (scFab), diabodies, anti-idiotypic (anti-Id) antibodies, or antigen-binding fragments of any of the above. Antibodies provided herein include members of any immunoglobulin type (e.g., IgG, IgM, IgD, IgE, IgA and IgY), any class (e.g. IgG1, IgG2, IgG3, IgG4, IgA1 and IgA2) or subclass (e.g., IgG2a and IgG2b).

As used herein, an "antibody fragment" or "antigen-binding fragment" of an antibody refers to any portion of a full-length antibody that is less than full length but contains at least a portion of the variable region of the antibody that binds antigen (e.g. one or more CDRs and/or one or more antibody combining sites) and thus retains the binding specificity, and at least a portion of the specific binding ability of the full-length antibody. Hence, an antigen-binding fragment refers to an antibody fragment that contains an antigen-binding portion that binds to the same antigen as the antibody from which the antibody fragment is derived. Antibody fragments include antibody derivatives produced by enzymatic treatment of full-length antibodies, as well as synthetically, e.g. recombinantly produced derivatives. An antibody fragment is included among antibodies. Examples of antibody fragments include, but are not limited to, Fab, Fab', F(ab')$_2$, single-chain Fv (scFv), Fv, dsFv, diabody, Fd and Fd' fragments and other fragments, including modified fragments (see, for example, Methods in Molecular Biology, Vol 207: Recombinant Antibodies for Cancer Therapy Methods and Protocols (2003); Chapter 1; p 3-25, Kipriyanov). The fragment can include multiple chains linked together, such as by disulfide bridges and/or by peptide linkers. An antibody fragment generally contains at least or about 50 amino acids and typically at least or about 200 amino acids. An antigen-binding fragment includes any antibody fragment that when inserted into an antibody framework (such as by replacing a corresponding region) results in an antibody that immunospecifically binds (i.e. exhibits Ka of at least or at least about $10^7$-$10^8$ M$^{-1}$) to the antigen.

As used herein, a "neutralizing antibody" is any antibody or antigen-binding fragment thereof that binds to a pathogen and interferes with the ability of the pathogen to infect a cell and/or cause disease in a subject.

As used herein, "monoclonal antibody" refers to a population of identical antibodies, meaning that each individual antibody molecule in a population of monoclonal antibodies is identical to the others. This property is in contrast to that of a polyclonal population of antibodies, which contains antibodies having a plurality of different sequences. Monoclonal antibodies can be produced by a number of well-known methods (Smith et al. (2004) *J. Clin. Pathol.* 57, 912-917; and Nelson et al., *J Clin Pathol* (2000), 53, 111-117). For example, monoclonal antibodies can be produced by immortalization of a B cell, for example through fusion with a myeloma cell to generate a hybridoma cell line or by infection of B cells with virus such as EBV. Recombinant technology also can be used to produce antibodies in vitro from clonal populations of host cells by transforming the host cells with plasmids carrying artificial sequences of nucleotides encoding the antibodies.

As used herein, a "conventional antibody" refers to an antibody that contains two heavy chains (which can be denoted H and H') and two light chains (which can be denoted L and L') and two antibody combining sites, where each heavy chain can be a full-length immunoglobulin heavy chain or any functional region thereof that retains antigen-binding capability (e.g. heavy chains include, but are not limited to, $V_H$, chains $V_H$-$C_H$1 chains and $V_H$-$C_H$1-$C_H$2-$C_H$3 chains), and each light chain can be a full-length light chain or any functional region of (e.g. light chains include, but are not limited to, $V_L$ chains and $V_L$—$C_L$ chains). Each heavy chain (H and H') pairs with one light chain (L and L', respectively)

As used herein, a full-length antibody is an antibody having two full-length heavy chains (e.g. $V_H$—$C_H$1-$C_H$2-$C_H$3 or $V_H$—$C_H$1-$C_H$2-$C_H$3-$C_H$4) and two full-length light chains ($V_L$—$C_L$) and hinge regions, such as human antibodies produced naturally by antibody secreting B cells and antibodies with the same domains that are synthetically produced.

As used herein, a dsFv refers to an Fv with an engineered intermolecular disulfide bond, which stabilizes the $V_H$-$V_L$ pair.

As used herein, a Fab fragment is an antibody fragment that results from digestion of a full-length immunoglobulin with papain, or a fragment having the same structure that is produced synthetically, e.g. by recombinant methods. A Fab fragment contains a light chain (containing a $V_L$ and $C_L$) and another chain containing a variable domain of a heavy chain ($V_H$) and one constant region domain of the heavy chain ($C_H$1).

As used herein, a F(ab')$_2$ fragment is an antibody fragment that results from digestion of an immunoglobulin with pepsin at pH 4.0-4.5, or a fragment having the same structure that is produced synthetically, e.g. by recombinant methods. The F(ab')$_2$ fragment essentially contains two Fab fragments where each heavy chain portion contains an additional few amino acids, including cysteine residues that form disulfide linkages joining the two fragments.

As used herein, a Fab' fragment is a fragment containing one half (one heavy chain and one light chain) of the F(ab')$_2$ fragment.

As used herein, an scFv fragment refers to an antibody fragment that contains a variable light chain ($V_L$) and variable heavy chain ($V_H$), covalently connected by a polypeptide linker in any order. The linker is of a length such that the two variable domains are bridged without substantial interference. Exemplary linkers are (Gly-Ser)$_n$ residues with some Glu or Lys residues dispersed throughout to increase solubility.

As used herein, the term "epitope" refers to any antigenic determinant on an antigen to which the paratope of an antibody binds. Epitopic determinants typically contain chemically active surface groupings of molecules such as amino acids or sugar side chains and typically have specific three dimensional structural characteristics, as well as specific charge characteristics.

As used herein, a variable domain or variable region is a specific Ig domain of an antibody heavy or light chain that contains a sequence of amino acids that varies among different antibodies. Each light chain and each heavy chain has one variable region domain, $V_L$ and $V_H$, respectively. The variable domains provide antigen specificity, and thus are responsible for antigen recognition. Each variable region contains CDRs that are part of the antigen-binding site domain and framework regions (FRs).

As used herein, "antigen-binding domain," "antigen-binding site," "antigen combining site" and "antibody combining site" are used synonymously to refer to a domain within an antibody that recognizes and physically interacts with cognate antigen. A native conventional full-length antibody molecule has two conventional antigen-binding sites, each containing portions of a heavy chain variable region and portions of a light chain variable region. A conventional antigen-binding site contains the loops that connect the anti-parallel beta strands within the variable region domains. The antigen combining sites can contain other portions of the variable region domains. Each conventional antigen-binding site contains three hypervariable regions from the heavy chain and three hypervariable regions from the light chain. The hypervariable regions also are called complementarity-determining regions (CDRs).

As used herein, "hypervariable region," "HV," "complementarity-determining region" and "CDR" and "antibody CDR" are used interchangeably to refer to one of a plurality of portions within each variable region that together form an antigen-binding site of an antibody. Each variable region domain contains three CDRs, named CDR1, CDR2 and CDR3. The three CDRs are non-contiguous along the linear amino acid sequence, but are proximate in the folded polypeptide. The CDRs are located within the loops that join the parallel strands of the beta sheets of the variable domain. As described herein, one of skill in the art knows and can identify the CDRs based on Kabat or Chothia numbering (see e.g., Kabat, E. A. et al. (1991) *Sequences of Proteins of Immunological Interest*, Fifth Edition, U.S. Department of Health and Human Services, NIH Publication No. 91-3242, and Chothia, C. et al. (1987) *J. Mol. Biol.* 196:901-917).

As used herein, framework regions (FRs) are the domains within the antibody variable region domains that are located within the beta sheets; the FR regions are comparatively more conserved, in terms of their amino acid sequences, than the hypervariable regions.

As used herein, a "constant region" domain is a domain in an antibody heavy or light chain that contains a sequence of amino acids that is comparatively more conserved than that of the variable region domain. In conventional full-length antibody molecules, each light chain has a single light chain constant region ($C_L$) domain and each heavy chain contains one or more heavy chain constant region ($C_H$) domains, which include, $C_H$1, $C_H$2, $C_H$3 and $C_H$4. Full-length IgA, IgD and IgG isotypes contain $C_H$1, $C_H$2, $C_H$3 and a hinge region, while IgE and IgM contain $C_H$1, $C_H$2, $C_H$3 and $C_H$4. $C_H$1 and $C_L$ domains extend the Fab arm of the antibody molecule, thus contributing to the interaction with antigen and rotation of the antibody arms. Antibody constant regions can serve effector functions, such as, but not limited to, clearance of antigens, pathogens and toxins to which the antibody specifically binds, e.g., through interactions with various cells, biomolecules and tissues.

As used herein, a functional region of an antibody is a portion of the antibody that contains at least a $V_H$, $V_L$, $C_H$ (e.g. $C_H1$, $C_H2$ or $C_H3$), $C_L$ or hinge region domain of the antibody, or at least a functional region thereof.

As used herein, a functional region of a $V_H$ domain is at least a portion of the full $V_H$ domain that retains at least a portion of the binding specificity of the full $V_H$ domain (e.g. by retaining one or more CDR of the full $V_H$ domain), such that the functional region of the $V_H$ domain, either alone or in combination with another antibody domain (e.g. $V_L$ domain) or region thereof, binds to antigen. Exemplary functional regions of $V_H$ domains are regions containing the CDR1, CDR2 and/or CDR3 of the $V_H$ domain.

As used herein, a functional region of a $V_L$ domain is at least a portion of the full $V_L$ domain that retains at least a portion of the binding specificity of the full $V_L$ domain (e.g. by retaining one or more CDRs of the full $V_L$ domain), such that the function region of the $V_L$ domain, either alone or in combination with another antibody domain (e.g. $V_H$ domain) or region thereof, binds to antigen. Exemplary functional regions of $V_L$ domains are regions containing the CDR1, CDR2 and/or CDR3 of the $V_L$ domain.

As used herein, "specifically bind" or "immunospecifically bind" with respect to an antibody or antigen-binding fragment thereof are used interchangeably herein and refer to the ability of the antibody or antigen-binding fragment to form one or more noncovalent bonds with a cognate antigen, by noncovalent interactions between the antibody combining site(s) of the antibody and the antigen. The antigen can be an isolated antigen or presented in a virus. Typically, an antibody that immunospecifically binds (or that specifically binds) to a virus antigen or virus is one that binds to the virus antigen (or to the antigen in the virus or to the virus) with an affinity constant Ka of about or $1\times10^7$ $M^{-1}$ or $1\times10^8$ $M^{-1}$ or greater (or a dissociation constant (KO of $1\times10^{-7}$ M or $1\times10^{-8}$ M or less). Affinity constants can be determined by standard kinetic methodology for antibody reactions, for example, immunoassays, surface plasmon resonance (SPR) (Rich and Myszka (2000) *Curr Opin. Biotechnol* 11:54; Englebienne (1998) *Analyst.* 123:1599), isothermal titration calorimetry (ITC) or other kinetic interaction assays known in the art (see, e.g., Paul, ed., Fundamental Immunology, 2nd ed., Raven Press, New York, pages 332-336 (1989); see also U.S. Pat. No. 7,229,619 for a description of exemplary SPR and ITC methods for calculating the binding affinity of antibodies). Instrumentation and methods for real time detection and monitoring of binding rates are known and are commercially available (e.g., BiaCore 2000, Biacore AB, Upsala, Sweden and GE Healthcare Life Sciences; Malmqvist (2000) *Biochem. Soc. Trans.* 27:335).

As used herein, "polypeptide" refers to two or more amino acids covalently joined. The terms "polypeptide" and "protein" are used interchangeably herein.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al., *Molecular Biology of the Gene,* 4th Edition, 1987, The Benjamin/Cummings Pub. co., p. 224).

As used herein, "nucleic acid" refers to at least two linked nucleotides or nucleotide derivatives, including a deoxyribonucleic acid (DNA) and a ribonucleic acid (RNA), joined together, typically by phosphodiester linkages.

Sequence "identity" has an art-recognized meaning and the percentage of sequence identity between two nucleic acid or polypeptide molecules or regions can be calculated using published techniques. Sequence identity can be measured along the full length of a polynucleotide or polypeptide or along a region of the molecule. (See, e.g.: *Computational Molecular Biology,* Lesk, A. M., ed., Oxford University Press, New York, 1988; *Biocomputing: Informatics and Genome Projects,* Smith, D. W., ed., Academic Press, New York, 1993; *Computer Analysis of Sequence Data,* Part I, Griffin, A. M., and Griffin, H. G., eds., Humana Press, New Jersey, 1994; *Sequence Analysis in Molecular Biology,* von Heinje, G., Academic Press, 1987; and Sequence Analysis Primer, Gribskov, M. and Devereux, J., eds., M Stockton Press, New York, 1991). While there exist a number of methods to measure identity between two polynucleotide or polypeptides, the term "identity" is well known to skilled artisans (Carrillo, H. & Lipman, D., *SIAM J Applied Math* 48:1073 (1988)).

As used herein, "operably linked" with reference to nucleic acid sequences, regions, elements or domains means that the nucleic acid regions are functionally related to each other. For example, a promoter can be operably linked to nucleic acid encoding a polypeptide, whereby the promoter regulates or mediates the transcription of the nucleic acid.

As used herein, "expression" refers to the process by which polypeptides are produced by transcription and translation of polynucleotides. The level of expression of a polypeptide can be assessed using any method known in art, including, for example, methods of determining the amount of the polypeptide produced from the host cell. Such methods can include, but are not limited to, quantitation of the polypeptide in the cell lysate by ELISA, Coomassie blue staining following gel electrophoresis, Lowry protein assay and Bradford protein assay.

As used herein, a "host cell" is a cell that is used in to receive, maintain, reproduce and amplify a vector. A host cell also can be used to express the polypeptide encoded by the vector. The nucleic acid contained in the vector is replicated when the host cell divides, thereby amplifying the nucleic acids.

As used herein, a "vector" is a replicable nucleic acid from which one or more heterologous proteins can be expressed when the vector is transformed into an appropriate host cell. Reference to a vector includes those vectors into which a nucleic acid encoding a polypeptide or fragment thereof can be introduced, typically by restriction digest and ligation. Reference to a vector also includes those vectors that contain nucleic acid encoding a polypeptide. The vector is used to introduce the nucleic acid encoding the polypeptide into the host cell for amplification of the nucleic acid or for expression/display of the polypeptide encoded by the nucleic acid. The vectors typically remain episomal, but can be designed to effect integration of a gene or portion thereof into a chromosome of the genome. Also contemplated are vectors that are artificial chromosomes, such as yeast artificial chromosomes and mammalian artificial chromosomes. Selection and use of such vehicles are well known to those of skill in the art.

As used herein, a vector also includes "virus vectors" or "viral vectors." Viral vectors are engineered viruses that are operatively linked to exogenous genes to transfer (as vehicles or shuttles) the exogenous genes into cells.

As used herein, an "expression vector" includes vectors capable of expressing DNA that is operatively linked with regulatory sequences, such as promoter regions, that are capable of effecting expression of such DNA fragments.

Such additional segments can include promoter and terminator sequences, and optionally can include one or more origins of replication, one or more selectable markers, an enhancer, a polyadenylation signal, and the like. Expression vectors are generally derived from plasmid or viral DNA, or can contain elements of both. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome.

As used herein, "treating" a subject with a disease or condition means that the subject's symptoms are partially or totally alleviated, or remain static following treatment. Hence treatment encompasses prophylaxis, therapy and/or cure. Prophylaxis refers to prevention of a potential disease and/or a prevention of worsening of symptoms or progression of a disease. Treatment also encompasses any pharmaceutical use of any antibody or antigen-binding fragment thereof provided or compositions provided herein.

As used herein, a "therapeutic effect" means an effect resulting from treatment of a subject that alters, typically improves or ameliorates the symptoms of a disease or condition or that cures a disease or condition.

As used herein, a "therapeutically effective amount" or a "therapeutically effective dose" refers to the quantity of an agent, compound, material, or composition containing a compound that is at least sufficient to produce a therapeutic effect following administration to a subject. Hence, it is the quantity necessary for preventing, curing, ameliorating, arresting or partially arresting a symptom of a disease or disorder.

As used herein, a "prophylactically effective amount" or a "prophylactically effective dose" refers to the quantity of an agent, compound, material, or composition containing a compound that when administered to a subject, will have the intended prophylactic effect, e.g., preventing or delaying the onset, or reoccurrence, of disease or symptoms, reducing the likelihood of the onset, or reoccurrence, of disease or symptoms, or reducing the incidence of viral infection. The full prophylactic effect does not necessarily occur by administration of one dose, and can occur only after administration of a series of doses. Thus, a prophylactically effective amount can be administered in one or more administrations.

Anti-HIV-1 Antibodies

The inventors isolated a monoclonal antibody from an HIV-1-infected Chinese donor sample and found that it has broadly neutralizing activities on a number of HIV-1 isolates. This monoclonal antibody is named DRVIA7. Sequence alignment and structural comparison revealed that antibody DRVIA7 and VRC01-like antibodies are highly similar in terms of structure, which suggests that DRVIA7 may be a VRC01-like antibody. The inventors further established an antibody heavy chain gene repertoire from a sample from the HIV-1 infected subject by using deep sequencing technology and then a large number of DRVIA7-like heavy chains were found by screening this repertoire. Heavy chain genes which are similar to DRVIA7 heavy chain were selected to produce new monoclonal antibodies by pairing with VRC01LC, from which several broadly neutralizing antibodies capable of blocking the entry of HIV-1 into target cells were obtained.

In one aspect, the present invention provides an isolated human monoclonal antibody comprising a heavy chain variable domain and a light chain variable domain, wherein the heavy chain variable domain comprises:

(i) VHCDR1, VHCDR2, and VHCDR3 respectively corresponding to VHCDR1, VHCDR2, and VHCDR3 contained in the amino acid sequence of SEQ ID NO:2, (ii) VHCDR1, VHCDR2, and VHCDR3 respectively corresponding to VHCDR1, VHCDR2, and VHCDR3 contained in the amino acid sequence of SEQ ID NO:4, or (iii) VHCDR1, VHCDR2, and VHCDR3 respectively corresponding to VHCDR1, VHCDR2, and VHCDR3 contained in the amino acid sequence of SEQ ID NO:6, and wherein the light chain variable domain comprises VLCDR1, VLCDR2, and VLCDR3 respectively corresponding to VLCDR1, VLCDR2, and VLCDR3 contained in the amino acid sequence of SEQ ID NO:10, and wherein the antibody is a neutralizing antibody which specifically binds to gp120 of HIV-1.

In some embodiments, the heavy chain variable domain comprises:

(i) VHCDR1, VHCDR2, and VHCDR3 respectively corresponding to amino acids 31-35, 50-66, and 99-109 of SEQ ID NO:2, (ii) VHCDR1, VHCDR2, and VHCDR3 respectively corresponding to amino acids 31-35, 50-66, and 99-109 of SEQ ID NO:4, or (iii) VHCDR1, VHCDR2, and VHCDR3 respectively corresponding to amino acids 31-35, 50-66, and 99-109 of SEQ ID NO:6.

In some embodiments, the light chain variable domain comprises VLCDR1, VLCDR2, and VLCDR3 respectively corresponding to amino acids 24-32, 48-54, and 87-91 of SEQ ID NO:10.

As used herein, when referring to the antibody of the invention, the expression "the heavy chain variable domain comprises VHCDR1 corresponding to VHCDR1 contained in the amino acid sequence of SEQ ID NO:2" means VHCDR1 in the heavy chain variable domain of said antibody has the same amino acid sequence with that of VHCDR1 contained in the amino acid sequence of SEQ ID NO:2. For example, as determined based on the Kabat numbering, VHCDR1 of antibody DRVIA7 consists of amino acids 31-35 (SSFIH) of the heavy chain variable domain as shown in SEQ ID NO:2, thus, the above expression means VHCDR1 of the heavy chain variable domain of the antibody of the invention also consists of SSFIH.

As used herein, when referring to the antibody of the invention, the expression "the light chain variable domain comprises VLCDR1 corresponding to VLCDR1 contained in the amino acid sequence of SEQ ID NO:10" means VLCDR1 in the light chain variable domain of said antibody has the same amino acid sequence with that of VLCDR1 contained in the amino acid sequence of SEQ ID NO:10. For example, as determined based on the Kabat numbering, VLCDR1 of antibody VRC01 consists of amino acids 24-32 (RTSQYGSLA) of the light chain variable domain as shown in SEQ ID NO:10, thus, the above expression means VLCDR1 of the light chain variable domain of the antibody of the invention also consists of RTSQYGSLA.

As used herein, VHCDR, HCDR, and CDRH have the same meaning and can be used interchangeably to refer to a complementary determining region of the antibody heavy chain variable domain. Likewise, VLCDR, LCDR, and CDRL have the same meaning and can be used interchangeably to refer to a complementary determining region of the antibody light chain variable domain.

In some embodiments, the heavy chain variable domain comprises an amino acid sequence of SEQ ID NO:2, 4 or 6 or an amino acid sequence having at least 85%, at least 90%, at least 95% or even higher sequence identity with SEQ ID NO:2, 4 or 6. Alternatively, the heavy chain variable domain consists of an amino acid sequence of SEQ ID NO:2, 4 or 6 or an amino acid sequence having at least 85%, at least 90%, at least 95% or even higher sequence identity with SEQ ID NO:2, 4 or 6. In some embodiments, the heavy chain variable domain comprises an amino acid sequence having about 90%, about 91%, about 92%, about 93%, about 94%, about 95%, about 96%, about 97%, about 98%, or about 99% sequence identity with SEQ ID NO:2, 4 or 6. In some preferred embodiments, the heavy chain variable domain comprises VHCDR1, VHCDR2, and VHCDR3 as set out in Table 1.

TABLE 1

VH/VL sequences and CDRs of exemplary antibodies of the invention (based on the Kabat numbering)

| | | |
|---|---|---|
| VL | EIVLTQSPGTLSLSPGETAIISCRTSQYGSLAWYQ<br>　　　　　　　　　　　　　　　CDR1<br>QRPGQAPRLVIYSGSTRAAGIPDRFSGSRWGPDYN<br>　　　　　　　　CDR2<br>LTISNLESGDFGVYYCQQYEFFGQGTKVQVDIKRT<br>　　　　　　　　　CDR3 | SEQ ID<br>NO: 10 |
| VH | QVQLVESGTQFRRPGASVRLSCEASGYTFISSFIH<br>　　　　　　　　　　　　　　　　　CDR1<br>WIRQGPGQGLEWMGWMNPRHGAVNYPRRFQGKVTM<br>　　　　　　　　　　CDR2<br>TRDTSIDTAYMELRDLRSDDTAMYFCVTSRTKDYD<br>　　　　　　　　　　　　　　　　CDR3<br>WDFVWGQGTLVVVSS | SEQ ID<br>NO: 2 |
| | QKQLVQSGTQFKRPGASVRLSCEASGYTFISSFIH<br>　　　　　　　　　　　　　　　　　CDR1<br>WIRQGPGQGLEWMGWMNPRHGGVNYPRRFQGKVTM<br>　　　　　　　　　　CDR2<br>TRDTSIDTAYMELRDLRSDDTAMYFCVTSRTKDYD<br>　　　　　　　　　　　　　　　　CDR3<br>WDFVWGQGTLVVVSS | SEQ ID<br>NO: 4 |
| | QRQLVQSGTQFKRPGASVRLSCEASGYTFISSFIH<br>　　　　　　　　　　　　　　　　　CDR1<br>WIRQAPGQGLEWMGWMNPRHGAVNYPRRFQGKVTM<br>　　　　　　　　　　CDR2<br>SRDTSIDTAYMELRDLRADDTATYFCVTSRTNDYD<br>　　　　　　　　　　　　　　　　CDR3<br>WDFVWGQGTLVVVSS | SEQ ID<br>NO: 6 |

In some embodiments, the light chain variable domain comprises an amino acid sequence of SEQ ID NO:10 or an amino acid sequence having at least 85%, at least 90%, at least 95% or even higher sequence identity with SEQ ID NO:10. Alternatively, the light chain variable domain consists of an amino acid sequence of SEQ ID NO:10 or an amino acid sequence having at least 85%, at least 90%, at least 95% or even higher sequence identity with SEQ ID NO:10. In some embodiments, the light chain variable domain comprises an amino acid sequence having about 90%, about 91%, about 92%, about 93%, about 94%, about 95%, about 96%, about 97%, about 98%, or about 99% sequence identity with SEQ ID NO:10. In some preferred embodiments, the light chain variable domain comprises VLCDR1, VLCDR2, and VLCDR3 as set out in Table 1.

In some embodiments, the antibody of the invention is IgG. In some other embodiments, the antibody of the invention is IgM. In some other embodiments, the antibody of the invention is IgA.

The present invention further provides an isolated antibody fragment, which is a functional fragment of the above described antibody of the invention and capable of specifically binding to gp120 of HIV-1. In some embodiments, the antibody fragment of the invention is selected from the group consisting of a Fab fragment, a Fab' fragment, a F(ab')2 fragment, a single chain Fv protein (scFv), and a disulfide stabilized Fv protein (dsFv). Preferably, the antibody fragment of the invention has broadly neutralizing activities against a number of HIV-1 isolates.

Polypeptides

The present invention also provides an isolated polypeptide which is the heavy chain variable domain of immunoglobulin. The polypeptide of the invention can be used to construct an antibody capable of specifically binding to gp120 of HIV-1 and having broadly neutralizing activities on HIV-1. In some embodiments, the polypeptide comprises VHCDR1, VHCDR2, and VHCDR3 respectively corresponding to amino acids 31-35, 50-66, and 99-109 of SEQ ID NO:2. In some other embodiments, the polypeptide comprises an amino acid sequence having about 90%, about 91%, about 92%, about 93%, about 94%, about 95%, about 96%, about 97%, about 98%, or about 99% sequence identity with SEQ ID NO:2. In some embodiments, the polypeptide comprises VHCDR1, VHCDR2, and VHCDR3 respectively corresponding to amino acids 31-35, 50-66, and 99-109 of SEQ ID NO:4. In some other embodiments, the polypeptide comprises an amino acid sequence having about 90%, about 91%, about 92%, about 93%, about 94%, about 95%, about 96%, about 97%, about 98%, or about 99% sequence identity with SEQ ID NO:4. In some embodiments, the polypeptide comprises VHCDR1, VHCDR2, and VHCDR3 respectively corresponding to amino acids 31-35, 50-66, and 99-109 of SEQ ID NO:6. In some other embodiments, the polypeptide comprises an amino acid sequence having about 90%, about 91%, about 92%, about 93%, about 94%, about 95%, about 96%, about 97%, about 98%, or about 99% sequence identity with SEQ ID NO:6.

Nucleic Acids, Vectors and Method for Producing Antibodies

In another aspect, the present invention provides an isolated nucleic acid molecule encoding an antibody or antibody fragment or polypeptide of the invention. In some embodiments, the nucleic acid molecule of the invention is operatively linked to a promoter.

The present invention also provides an expression vector comprising at least one nucleic acid molecule of the invention as described above.

The present invention also provides an isolated host cell which has been transformed with at least one nucleic acid molecule or expression vector of the invention as described above.

In another aspect, the present invention provides a method of producing an antibody, comprising:

(i) transforming a host cell with at least one nucleic acid molecule or expression vector of the invention as described above, (ii) culturing the transformed host cell under conditions suitable for the expression of the nucleic acid molecule or the expression vector, and (iii) isolating and purifying the antibody or antibody fragment expressed from the nucleic acid molecule or the expression vector.

The present invention also relates to an isolated antibody or antibody fragment obtained by performing the method of the invention as described above, which is capable of specifically binding to HIV-1 gp120. Preferably, the isolated antibody or antibody fragment obtained by the method of the invention has broadly neutralizing activities on various HIV-1 isolates.

Detection and Diagnosis

In another aspect, the present invention provides a method of detecting an HIV-1 infection in a human subject, comprising:

(i) contacting a biological sample from the subject with an antibody or antibody fragment of the invention, and (ii) determining the presence of an immune complex formed by the antibody or the antibody fragment in said sample, wherein the presence of said immune complex indicates that the subject has an HIV-1 infection.

In some embodiments of the method of the invention for detecting an HIV-1 infection in a human subject, in step (i), the sample is immobilized on a solid substrate prior to the contacting, and the contacting comprises applying the antibody or antibody fragment to the solid substrate on which the sample is immobilized. In some embodiments, the antibody or antibody fragment is labeled with a fluorescent, enzymatic, or radioactive label. In some other embodiments, in step (ii), the solid substrate is brought into contact with a first binding partner capable of specifically binding to the antibody or antibody fragment. In some embodiments, the first binding partner is a second antibody capable of specifically binding to the antibody or antibody fragment.

In some other embodiments of the method of the invention for detecting an HIV-1 infection in a human subject, in step (i), the antibody or antibody fragment is immobilized on a solid substrate prior to the contacting, and the contacting comprises applying the sample to the solid substrate on which the antibody or antibody fragment is immobilized. In some embodiments, in step (ii), the solid substrate is brought into contact with a second binding partner capable of specifically binding to an antigen of HIV-1. In some embodiments, the second binding partner is a second antibody capable of specifically binding to an antigen of HIV-1. In some embodiments, the second antibody is capable of specifically binding to gp120 of HIV-1. In some embodiments, the antibody or antibody fragment and the second antibody capable of specifically binding to an antigen of HIV-1 bind to different epitopes on HIV-1.

In some embodiments of the method of the invention for detecting an HIV-1 infection in a human subject, the biological sample from the subject is a blood, plasma, serum, blood cell, or blood cell lysate sample.

In some embodiments of the method of the invention for detecting an HIV-1 infection in a human subject, the biological sample from the subject contains blood cells, and the method further comprises, prior to, during, or after step (i), contacting the biological sample with a third binding partner capable of specifically binding to the blood cells. In some embodiments, the third binding partner is an antibody capable of specifically binding to the blood cells. In some specific embodiments, the blood cells are lymphocytes, for example T cells, such as CD4+ T cells. In some other specific embodiments, the blood cells are monocytes. In some specific embodiments, the third binding partner is an antibody capable of specifically binding to a marker on the blood cells which is characteristic for the blood cells.

In another aspect, the present invention relates to use of the antibody or antibody fragment of the invention in manufacture of a kit for detecting an HIV-1 infection in a human subject.

In another aspect, the present invention also provides a kit for detecting an HIV-1 infection in a human subject, comprising an antibody or antibody fragment of the invention.

Treatment and Pharmaceutical Composition

In another aspect, the present invention also provides a method of preventing or treating an HIV-1 infection in a human subject, comprising administering to the subject an effective amount of an antibody or antibody fragment or a pharmaceutical composition of the invention. In some embodiments, the subject has acquired immune deficiency syndrome (AIDS). In some embodiments, the method further comprises administering to the subject at least one anti-viral agent against HIV-1.

A subject or candidate for treatment with an antibody or antigen-binding fragment thereof provided herein includes, but is not limited to, a human subject that has been exposed to a HIV-1 virus, a human subject who exhibits one or more symptoms of a HIV-1 infection and a human subject who is at risk of a HIV-1 infection.

In another aspect, the present invention also relates to use of the antibody or antibody fragment of the invention in manufacture of a pharmaceutical composition for preventing or treating an HIV-1 infection in a human subject. In some embodiments, the subject has acquired immune deficiency syndrome (AIDS).

In another aspect, the present invention provides a pharmaceutical composition, which comprises at least one antibody or antibody fragment of the invention as described above, and a pharmaceutically acceptable carrier.

An effective amount of antibody or antigen-binding fragment thereof to be administered therapeutically will depend, for example, upon the therapeutic objectives, the route of administration, and the condition of the patient. In addition, the attending physician takes into consideration various factors known to modify the action of drugs, including severity and type of disease, patient's health, body weight, sex, diet, time and route of administration, other medications and other relevant clinical factors. Accordingly, it will be necessary for the therapist to titer the dosage of the antibody or antigen-binding fragment thereof and modify the route of administration as required to obtain the optimal therapeutic effect. Typically, the clinician will administer the antibody or antigen-binding fragment thereof until a dosage is reached that achieves the desired effect. The progress of this therapy is easily monitored by conventional assays. Exemplary assays for monitoring treatment of a viral infection are know in the art and include for example, viral titer assays.

Generally, the dosage ranges for the administration of the antibodies or antigen-binding fragments thereof provided herein are those large enough to produce the desired effect in which the symptom(s) of the pathogen-mediated disease (e.g. viral disease) are ameliorated or the likelihood of virus infection is decreased. In some examples, the antibodies or antigen-binding fragments thereof provided herein are administered in an amount effective for inducing an immune response in the subject. The dosage is not so large as to cause adverse side effects, such as hyperviscosity syndromes, pulmonary edema or congestive heart failure. Generally, the dosage will vary with the age, condition, sex and the extent of the disease in the patient and can be determined by one of skill in the art. The dosage can be adjusted by the individual physician in the event of the appearance of any adverse side effect. Exemplary dosages for the prevention or treatment of a HIV-1 infection include, but are not limited to, about or 0.01 mg/kg to about or 300 mg/kg, such as for example, about or 0.01 mg/kg, about or 0.1 mg/kg, about or 0.5 mg/kg, about or 1 mg/kg, about or 5 mg/kg, about or 10 mg/kg, about or 15 mg/kg, about or 20 mg/kg, about or 25 mg/kg, about or 30 mg/kg, about or 35 mg/kg, about or 40 mg/kg, about or 45 mg/kg, about or 50 mg/kg, about or 100 mg/kg, about or 150 mg/kg, about or 200 mg/kg, about or 250 mg/kg, or about or 300 mg/kg.

For treatment of a viral infection, the dosage of the antibodies or antigen-binding fragments thereof of the invention can vary depending on the type and severity of the disease. The antibodies or antigen-binding fragments thereof can be administered single dose, in multiple separate administrations, or by continuous infusion. For repeated administrations over several days or longer, depending on the condition, the treatment can be repeated until a desired suppression of disease symptoms occurs or the desired improvement in the patient's condition is achieved. Repeated administrations can include increased or decreased amounts of the antibody or antigen-binding fragment thereof depending on the progress of the treatment. Other dosage regimens also are contemplated.

The antibodies or antigen-binding fragments thereof provided herein can be administered to a subject by any method known in the art for the administration of polypeptides, including for example systemic or local administration. The antibodies or antigen-binding fragments thereof can be administered by routes, such as parenteral (e.g., intradermal, intramuscular, intraperitoneal, intravenous, subcutaneous, or intracavity), topical, epidural, or mucosal (e.g. intranasal or oral). The antibodies or antigen-binding fragments thereof can be administered externally to a subject, at the site of the disease for exertion of local or transdermal action. Compositions containing the antibodies or antigen-binding fragments thereof can be administered by any convenient route, for example by infusion or bolus injection, by absorption through epithelial or mucocutaneous linings (e.g., oral mucosa, rectal and intestinal mucosa).

Pharmaceutical compositions provided herein can be in various forms, e.g., in solid, semi-solid, liquid, powder, aqueous, or lyophilized form. Examples of suitable pharmaceutically acceptable carriers are known in the art and include but are not limited to water, buffering agents, saline solutions, phosphate buffered saline solutions, various types of wetting agents, sterile solutions, alcohols, gum arabic, vegetable oils, benzyl alcohols, gelatin, glycerin, carbohydrates such as lactose, sucrose, amylose or starch, magnesium stearate, talc, silicic acid, viscous paraffin, perfume oil, fatty acid monoglycerides and diglycerides, pentaerythritol fatty acid esters, hydroxy methylcellulose, powders, among others. Pharmaceutical compositions provided herein can contain other additives including, for example, antioxidants, preservatives, antimicrobial agents, analgesic agents, binders, disintegrants, coloring, diluents, excipients, extenders, glidants, solubilizers, stabilizers, tonicity agents, vehicles, viscosity agents, flavoring agents, emulsions, such as oil/water emulsions, emulsifying and suspending agents, such as acacia, agar, alginic acid, sodium alginate, bentonite, carbomer, carrageenan, carboxymethylcellulose, cellulose, cholesterol, gelatin, hydroxyethyl cellulose, hydroxypropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, and miscellaneous ingredients such as crystalline cellulose, microcrystalline cellulose, citric acid, dextrin, dextrose, liquid glucose, lactic acid, lactose, magnesium chloride, potassium metaphosphate, starch, among others (see, generally, Alfonso R. Gennaro (2000) Remington: The Science and Practice of Pharmacy, 20th Edition. Baltimore, Md.: Lippincott Williams & Wilkins). Such carriers and/or additives can be formulated by conventional methods and can be administered to the subject at a suitable dose. Stabilizing agents such as lipids, nuclease inhibitors, polymers, and chelating agents can preserve the compositions from degradation within the body.

The following examples are illustrative and should not be construed to limit the scope of the invention in any way.

EXAMPLES

Example 1: Identification of Broadly Neutralizing Antibody DRVIA7

The Isolation of Antibody DRVIA7 from an HIV-1-Infected Chinese Donor

A monoclonal antibody DRVIA7 was isolated from a sample from an HIV-1-infected Chinese donor and has been identified as having broadly neutralizing activities against HIV-1 isolates. Two Escherichia coli strains carrying the heavy chain gene expression vector (DRVIA7H) or light chain gene expression vector (DRVIA7L) were deposited at China General Microbiological Culture Collection Center (CGMCC) (NO.1 West Beichen Road, Chaoyang District, Beijing, China) under the accession number of CGMCC No. 11879 and CGMCC No. 11880, respectively. The sequence encoding the heavy chain variable region contained in DRVIA7H is SEQ ID NO:1, and the encoded amino acid sequence of the heavy chain variable region is SEQ ID NO:2. Table 1 shows the sequence of variable region and CDRs of DRVIA7 heavy chain. The sequence encoding the light chain variable region contained in DRVIA7L is SEQ ID NO:7, and the encoded amino acid sequence of the light chain variable region is SEQ ID NO:8.

The Expression and Purification of Antibody DRVIA7

Escherichia coli strains carrying the heavy chain gene expression vector DRVIA7H or the light chain gene expression vector DRVIA7L were separately inoculated in 100 ml LB culture medium (Amersham) containing kanamycin at a final concentration of 50 μg/ml, and then cultured at 37° C. for 16 hours with shaking at 200 rpm. The expression vector plasmids were extracted from the cultures using Plasmid Midi Kit (Omega) following the manufacturer's instructions. 293F cells were co-transfected with equal amount of heavy and light chain plasmids using PEI transfection reagent (Polysciences), and then cultured at 8% $CO_2$ and 37° C. for 6 days. Monoclonal antibody DRVIA7 was purified from the culture supernatant using Protein-A columns (GE health), and the concentration of antibody was determined by NanoDrop2000 (Thermo). The purified antibody samples were stored at 4° C. for further detection.

Neutralizing Activity of Antibody DRVIA7

The neutralizing activity of antibody DRVIA7 was measured using TZM-bl/pseudovirus neutralizing assay[7]. Briefly, antibody DRVIA7 was serially diluted in DMEM growth medium (Hyclone). The diluted antibody (100 μl/well) and the pseudovirus (50 μl/well, containing pseudovirus of 200 $TCID_{50}$) were added to each well of the 96-well flat bottom plates. The plates were then incubated at 37° C., 5% $CO_2$ for 1 hour. TZM-bl cells were added at $1 \times 10^4$/well to the plates in DMEM growth medium containing 11 μg/ml DEAE-dextran (Sigma). Cell controls (TZM-bl cell only) and virus controls (TZM-bl and pseudovirus) were set. The plates were then incubated at 37° C., 5% $CO_2$ for 48 hours. The luciferase reaction was detected using Bright-Glo luciferase reagent kit (Promega) and the 50% inhibitory dose ($ID_{50}$) was calculated. As shown in Table 2, DRVIA7 can neutralize different subtypes of HIV-1 viruses, and thus is a broadly neutralizing antibody.

TABLE 2

Neutralization of DRVIA7 monoclonal antibody with virus panel of 8 isolates

| Clade | Virus ID | Tier | $IC_{50}$ (μg/ml) DRVIA7 |
|---|---|---|---|
| A | DJ263.8 | 1B | 0.07[ΔΔ] |
| A | Q168.a2 | 2 | 0.58 |
| B | HXBc2 | 1B | >20 |
| B | Bal.26 | 1B | 0.003 |
| B | JRCSF | 2 | >50 |
| B | JRFL | 2 | 0.90 |
| C | ZM109.4 | 1B | >20 |
| C | DU156.12 | 2 | >20 |

[ΔΔ]The neutralizing potency is measured as $IC_{50}$ in μg/ml of the monoclonal antibodies.

Sequence and Crystal Structure Analysis of Antibody DRVIA7

The sequence analysis of antibody DRVIA7 was performed using IMGT V-QEST server see the website of the international ImMunoGeneTics information system) assisted with manual inspection. The CDR3 length was determined based on the Kabat numbering. As shown in FIGS. 1A-1D, DRVIA7 heavy chain is derived from IgHV1-02*02 allele, and CDRH3 contains 11 amino acids. DRVIA7 light chain is derived from IgKV1-5*03 allele, and CDRL3 contains 5 amino acids. DRVIA7 heavy chain is derived from the same allele as VRC01 and CDRL3 of light chain has the same length as VRC01[1], suggesting that DRVIA7 may be a VRC01-like antibody.

Crystallographic characterization of unliganded DRVIA7 and DRVIA7+gp120 complex were determined using X-ray crystallography (Table 3). Ribbon diagrams of the crystal structure of DRVIA7 bound to gp120 was displayed in FIG. 2.

TABLE 3

X-ray crystallographic data collection and refinement statistics.

| Data collection | UnligandedDRVIA7 | DRVIA7 + gp120 complex |
|---|---|---|
| X-ray Source | APS 23ID-B | APS 23ID-B |
| Wavelength (Å) | 1.033 | 1.033 |
| Space group | P1 | $P4_12_12$ |
| Unit cell parameters | a = 66.8, b = 73.8, c = 101.2 Å | a = b = 72.3, c = 338.8 Å |
| | α = 89.8°, β = 89.4°, γ = 90.0° | α = β = γ = 90.0° |
| Resolution (Å) | 50.0-2.90 (2.95-2.90)[a] | 29.0-3.39 (3.67-3.39)[a] |
| Observations | 74,827 | 205,736 |
| Unique reflections | 41,586 (2,062)[a] | 13,362 (2,662)[a] |
| Redundancy | 1.8 (1.8)[a] | 15.4 (15.7)[a] |
| Completeness (%) | 97.4 (98.4)[a] | 99.7 (99.3)[a] |
| $<I/\sigma_I>$[b] | 3.8 (1.1)[a] | 10.0 (1.2)[a] |
| $R_{sym}$[c] | 0.24 (0.89)[a] | 0.31 (2.92)[a] |
| $R_{pim}$[c] | 0.17 (0.63)[a] | 0.08 (0.76)[a] |
| $CC_{1/2}$ | 0.55[a] | 0.62[a] |
| Refinement statistics | | |
| Resolution (Å) | 49.54-2.90 (2.97-2.90)[a] | 28.97-3.40 (3.66-3.40)[a] |
| Reflections (work) | 39,396 (2,443)[a] | 12,585 (2,394)[a] |
| Reflections (test) | 2,109 (151)[a] | 653 (141)[a] |
| $R_{cryst}$(%)[c] | 23.4 (28.4)[a] | 25.3 (37.6)[a] |
| $R_{free}$(%)[d] | 28.4 (36.0)[a] | 30.6 (39.8)[a] |
| Average B-value (Å²) | 34 | 148 |
| DRVIA7 Fab | 34 | 126 |
| gp120 core | N/A | 174 |
| Wilson B-value (Å²) | 36 | 121 |
| RMSD from ideal geometry | | |
| Bond length (Å) | 0.005 | 0.006 |
| Bond angles (°) | 1.23 | 1.33 |
| Ramachandran statistics (%)[f] | | |
| Favored | 97.9 | 97.9 |
| Outliers | 0.0 | 0.0 |
| PDB ID | 5CD3 | 5CD5 |

[a] Numbers in parentheses refer to the highest resolution shell.

[b] Calculated as average(I)/average(σI)

[c] $R_{Sym} = \Sigma_{hkl}\Sigma_i | I_{hkl, i} - <I_{hkl}> |/\Sigma_{hkl} \Sigma_i I_{hkl, i}$, where $I_{hkl, i}$ is the scaled intensity of the $i^{th}$ measurement of reflection h, k, l, $<I_{hkl}>$ is the average intensity for that reflection, and n is the redundancy. $R_{pim}$ is a redundancy-independent measure of the quality of intensity measurements. $R_{pim} = \Sigma_{hkl} (1/(n-1))^{1/2} \Sigma_i | I_{hkl, i} - <I_{hkl}> |/\Sigma_{hkl}\Sigma_i I_{hkl, i}$, where $I_{hkl, i}$ is the scaled intensity of the $i^{th}$ measurement of reflection h, k, l, $<I_{hkl}>$ is the average intensity for that reflection, and n is the redundancy.

[d] $R_{cryst} = \Sigma_{khl} | F_o - F_c |/\Sigma_{hkl} | F_o | \times 100$

[e] $R_{free}$ was calculated as for $R_{cryst}$, but on a test set comprising 5% of the data excluded from refinement.

[f] These values were calculated using MolProbity(http://molprobity.biochem.duke.edu/).

Figure 3:
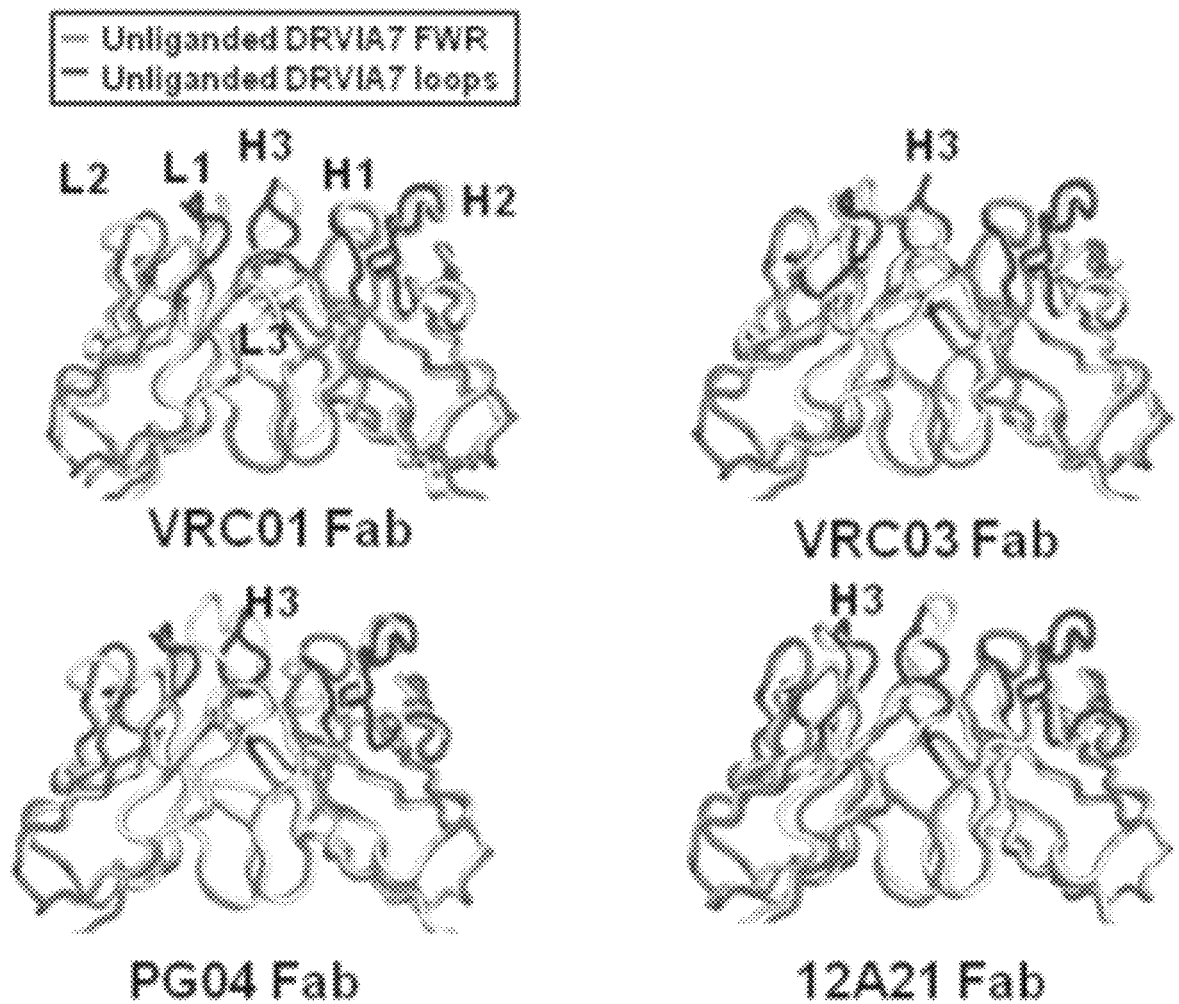
FIG. 3 shows the crystal structure of the antibody DRVIA7 compared with VRC01-like antibodies.

The crystal structure of DRVIA7 strongly resembles some published VRC01-like antibodies such as VRC01 (PDBID: 3NGB), VRC03 (PDBID: 3SE8), PG04 (PDBID: 3SE9) and 12A21 (PDBID: 4JPW) (FIG. 3). The results also suggest that DRVIA7 may be a VRC01-like antibody.

Example 2: Production and Functional Identification of Antibody DRVIA7H+VRC01L

The Expression and Purification of Antibody DRVIA7H+VRC01L

*Escherichia coli* strain carrying the heavy chain gene expression vector DRVIA7H was inoculated in 100 ml LB culture medium (Amersham) containing kanamycin at a final concentration of 50 μg/ml, and then cultured at 37° C. for 16 hours with shaking at 200 rpm. The expression vector plasmid was extracted from the culture using Plasmid Midi Kit (Omega) following the manufacturer's instructions. The polynucleotide encoding the variable region (SEQ ID NO:10) of VRC01 light chain (SEQ ID NO:9, GenBank: GU980703.1) was cloned into expression vector. 293F cells were co-transfected with equal amount of DRVIA7H expression vector and VRC01 light chain expression vector using PEI transfection reagent (Polysciences), and then cultured at 8% $CO_2$ and 37° C. for 6 days. Monoclonal antibody DRVIA7H+VRC01L was purified from the culture supernatant using Protein-A columns (GE health), and the concentration of antibody was determined by Nano-Drop2000 (Thermo). The purified antibody samples were stored at 4° C. for further detection.

Binding Capacity of Antibody DRVIA7H+VRC01L

Figure 4A:
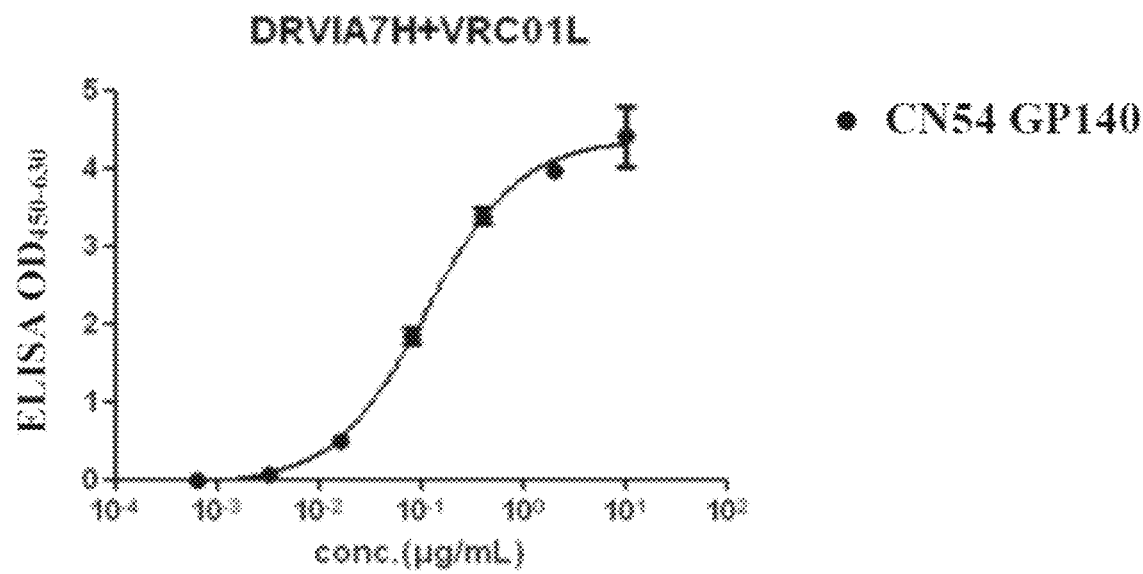
FIG. 4 shows the binding capacity of monoclonal antibodies to HIV-1 antigens. (A) The binding capacity of monoclonal antibody DRVIA7H+VRC01L to gp140. (B) The binding capacity of monoclonal antibody DRVIA7H+VRC01L to gp120. (C) The binding capacity of monoclonal antibody gDRVI01-H1+VRC01L to gp140. (D) The binding capacity of monoclonal antibody gDRVI01-H2+VRC01L to gp140.
Figure 4B:
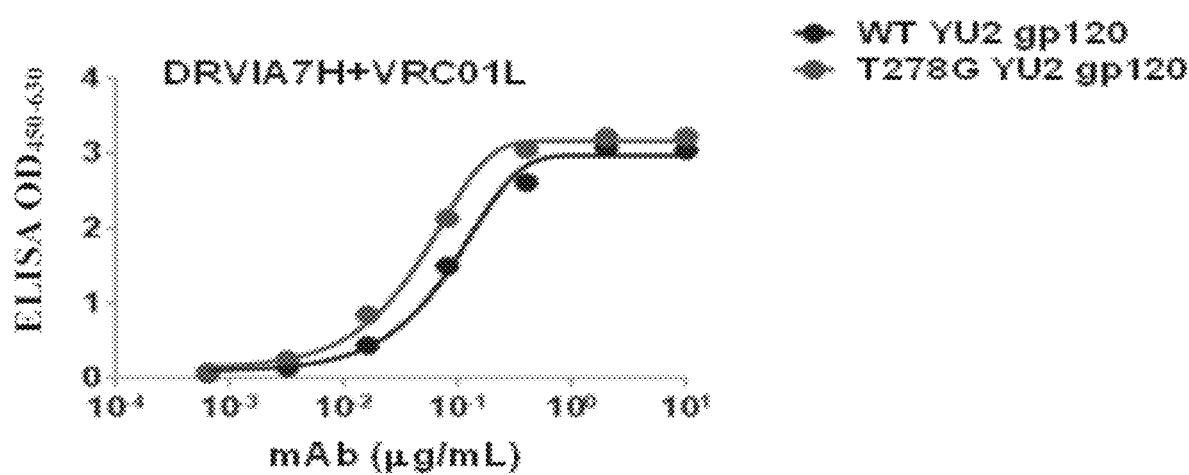
Figure 4C:
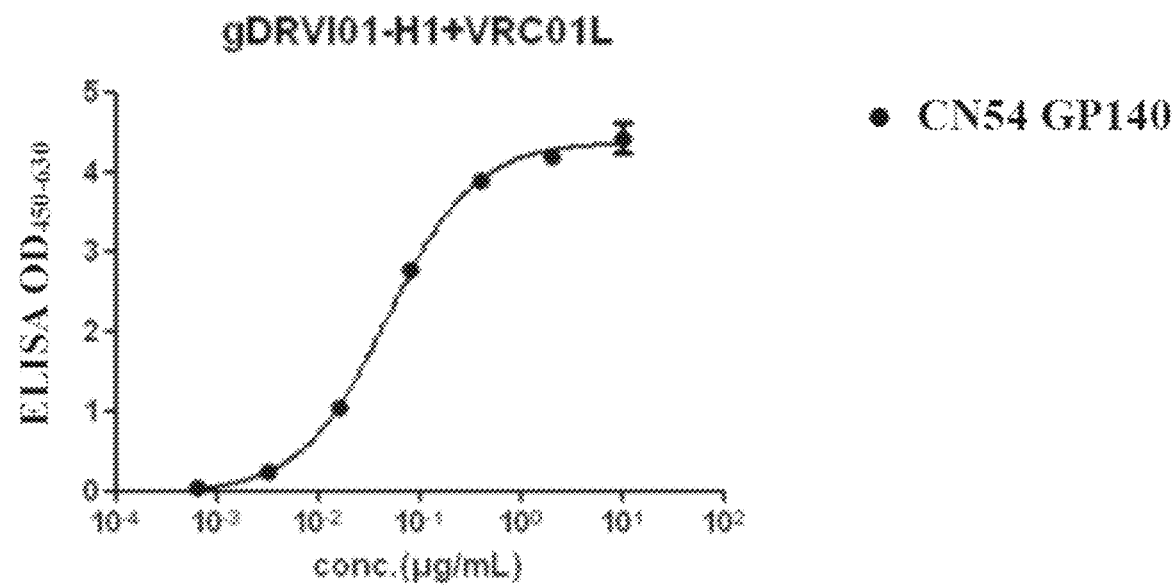
Figure 4D:
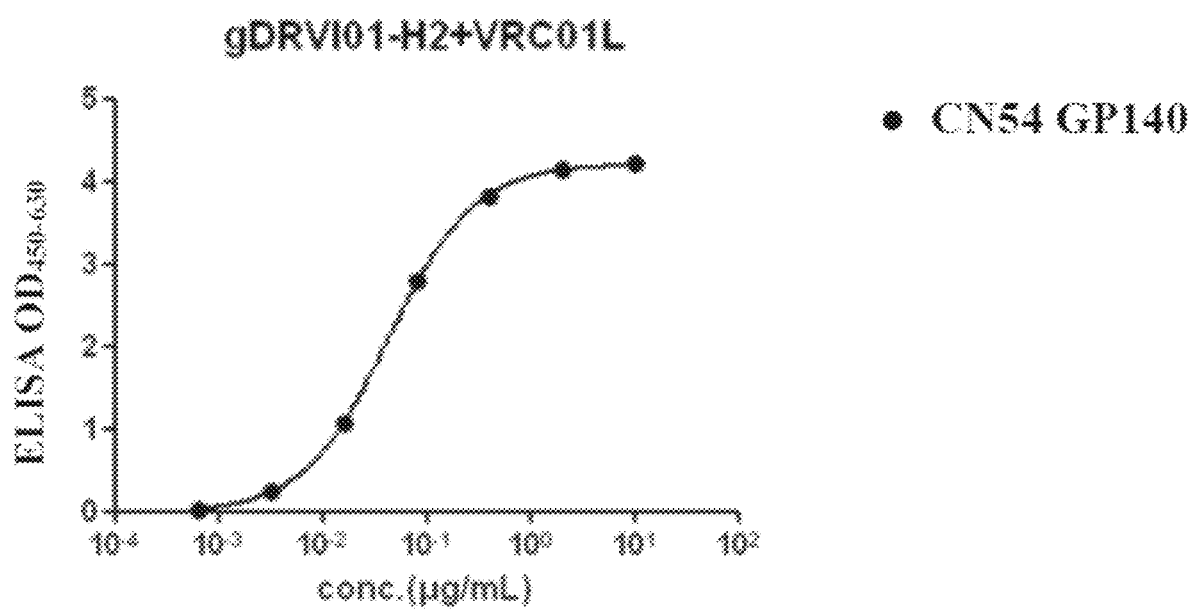
Figure 5:
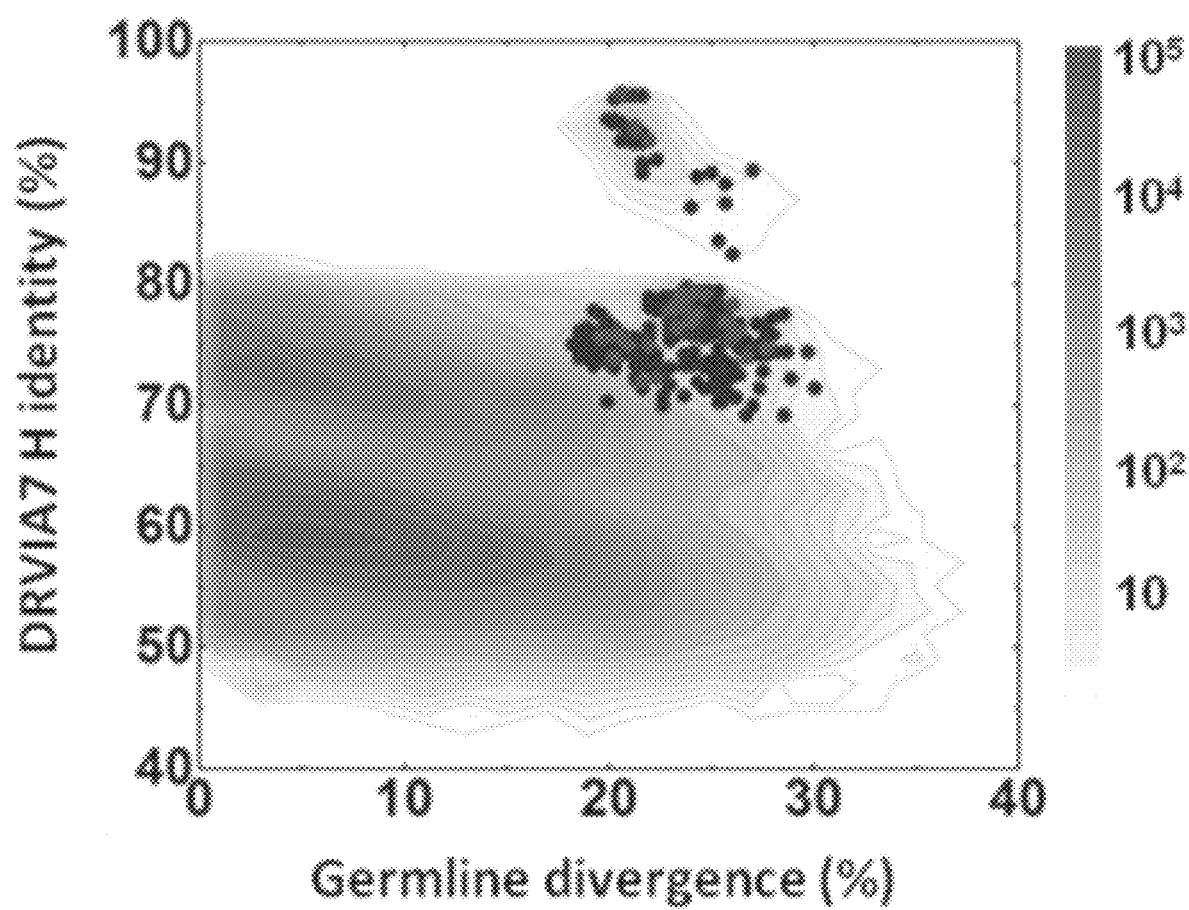
FIG. 5 shows the identity/divergence 2D analysis of the heavy chain repertoires from the HIV-1 infected donor.

The binding capacity of antibody DRVIA7H+VRC01L was detected by Enzyme Linked Immunosorbent Assay (ELISA). Briefly, 96-well flat-bottom plates were coated with either purified CN54 GP140, wild-type (WT) YU2 gp120 or T278G YU2 gp120 (YU2 gp120 with T278G mutation) protein at 2 μg/ml in PBS (100 μl/well) at 4° C. overnight. The plates were washed five times with 0.05% Tween 20 in PBS (PBS-T), and then blocked with 250 μl/well of blocking buffer (5% skim milk and 2% bovine albumin in PBS) for 1 h at RT. After three times of washing with PBS-T, 100 μl of antibody serially diluted (5-time dilution, starting from 10 μg/ml) in blocking buffer was added to the antigen-coated plates, and incubated at 37° C. for 1 hour. Plates were then washed five times with PBS-T, 100 μl of HRP conjugated goat anti-human IgG (H+L) (ZSGB-BIO) diluted at 1:5000 in blocking buffer was added and incubated at 37° C. for 1 h. The plates were washed five times with PBS-T and 100 μl TMB (Kinghawk) substrate was added and incubated for 20 mins at RT and the reaction was stopped by the addition of 50 μl 1N $H_2SO_4$ (Kinghawk) to each well and the readout (OD) was measured at a wave length of 450 nm and 630 nm. As shown in FIG. 4, monoclonal antibody DRVIA7H+VRC01L can specifically bind with CN54 GP140 protein (FIG. 4A) as well as wild-type and mutant gp120 proteins (FIG. 4B).

Neutralizing Activity of Antibody DRVIA7H+VRC01L

The neutralizing activity of DRVIA7H+VRC01L was measured using TZM-bl/pseudovirus neutralizing assay as described in Example 1. As shown in Tables 4A and 4B, DRVIA7H+VRC01L can neutralize different subtypes of HIV-1 viruses on Global Panel and DRVI Panel, and thus is a broadly neutralizing monoclonal antibody.

TABLE 4A

Neutralizing breadth and potency of three monoclonal antibodies on the global panel of HIV-1 Env strains.

| | Global Panel[a] | | monoclonal antibodies | | |
|---|---|---|---|---|---|
| Clade | Tier | Pseudo-virus | DRVIA7H + VRC01L | gDRVI01-H1 + VRC01L | gDRVI01-H2 + VRC01L |
| A | 2 | 398-F1 | 0.8[ΔΔ] | 0.71 | 0.6 |
| B | 2 | TRO.11 | 1.18 | 0.47 | 0.41 |
| | 2 | X2278 | 0.34 | 0.3 | 0.41 |
| C | 2 | 25710 | 2.5 | 0.93 | 0.52 |
| | 2 | Ce0217 | 0.65 | 0.53 | 0.63 |
| | 2 | Ce1176 | 4.08 | 2.41 | 2.9 |
| G | 2 | X1632 | 0.61 | 0.09 | 0.22 |
| CRF01_AE | 2 | CNE55 | 1.23 | 0.81 | 0.8 |
| | 2 | CNE8 | 1.48 | 0.69 | 0.51 |
| CRF07_BC | 2 | BJOX2000 | 15.89 | 1.19 | 1.41 |
| | 2 | CH119.10 | 1.85 | 0.76 | 0.59 |
| AC | 2 | 246 | 1.29 | 0.94 | 0.53 |
| | Potency(GMTs) | | 1.45 | 0.64 | 0.63 |
| | Breadth %(<20 μg/ml) | | 100[**] | 100 | 100 |

[a]The global panel was developed by the Montefiori group at Duke University Medical Center.

[ΔΔ]The neutralizing potency is measured as $IC_{50}$ in μg/ml of the monoclonal antibodies.

[**]The neutralizing breadth is calculated as the percentage of viruses neutralized with $IC_{50}$ <20 μg/ml.

TABLE 4B

Neutralizing breadth and potency of three monoclonal
antibodies on the DRVI panel of HIV-1 Env strains.

| DRVI Panel[a] | | | monoclonal antibodies | | |
|---|---|---|---|---|---|
| Clade | Tier | Pseudo-virus | DRVIA7H + VRC01L | gDRVI01-H1 + VRC01L | gDRVI01-H2 + VRC01L |
| B | 1A | SF162 | 0.3[ΔΔ] | 0.18 | 0.31 |
| | 2 | QH0692 | 2.03 | 2 | 1.45 |
| | 2 | SC422661 | 0.58 | 0.43 | 0.3 |
| | 3 | PV0.4 | 1.18 | 0.67 | 0.3 |
| | 2 | AC10 | 15.47 | 6.35 | 1.59 |
| | 2 | RHPA4259 | 0.34 | 0.13 | 0.09 |
| | 2 | REJO4541 | 0.75 | 0.2 | 0.26 |
| | 3 | TRJO4551 | 1.44 | 0.36 | 0.44 |
| | 2 | CAAN5342 | 3.4 | 1.75 | 1.69 |
| CRF07_BC | 2 | CH110 | 0.15 | 0.04 | 0.04 |
| | 2 | CH117 | 0.59 | 0.1 | 0.07 |
| | 2 | CH181 | 0.98 | 0.55 | 0.51 |
| | 3 | CH120 | 6.53 | 2.09 | 1.88 |
| C | 1A | MW965 | 0.2 | 0.15 | 0.17 |
| | 1B | ZM109F | 0.59 | 0.19 | 0.28 |
| | 2 | Du422 | >20 | 7 | 1.77 |
| | 2 | ZM249M | 0.74 | 0.35 | 0.22 |
| | 2 | CAP45 | 0.84 | 0.31 | 0.23 |
| A | 2 | Q461 | 1.4 | 0.85 | 1.01 |
| | 2 | Q769 | 0.3 | 0.18 | 0.09 |
| | 2 | Q259 | >20 | 4.33 | 2.15 |
| | 2 | Q842 | 0.18 | 0.08 | 0.09 |
| CRF01_AE | NA | BJMSM2249 | 2.25 | 1.01 | 0.97 |
| | NA | BJMSM2316 | 0.47 | 0.3 | 0.16 |
| | NA | BJMSM2498 | 4.32 | 1.37 | 1.23 |
| Potency(GMTs) | | | 0.91 | 0.5 | 0.38 |
| Breadth %(<20 μg/ml) | | | 92[☆☆] | 100 | 100 |

[a]The DRVI panel was compiled by the Shao group in the Department of Virology and Immunology at China CDC.

[ΔΔ]The neutralizing potency is measured as $IC_{50}$ in μg/ml of the monoclonal antibodies.

[☆☆]The neutralizing breadth is calculated as the percentage of viruses neutralized with $IC_{50}$ <20 μg/ml.

Example 3: Preparation of a Series of VRC01-Like Antibodies by Screening Antibody Heavy Chain Gene Repertoire

The Establishment of Antibody Heavy Chain Repertoire

The antibody heavy chain gene repertoire was established using deep sequencing technology from the blood sample of the HIV-1 infected donor from whom DRVIA7 was isolated, and a large number of DRVIA7-like light chain genes were found in this repertoire. As shown in FIG. 5, based on cross-donor phylogenetic analysis (CDPA), 530 VRC01-like heavy chains (blue dots) were identified and 30 candidate heavy chains (red dots) were synthesized and the binding capacity and neutralizing activity were tested.

Antibodies gDRVI01-H1+VRC01L and gDRVI01-H2+VRC01L

By pairing the above thirty candidate heavy chains with the light chain of VRC01, a series of antibodies were then prepared according to the expression and purification process as described Example 1, and binding and neutralizing assays were also performed. Two antibodies gDRVI01-H1+VRC01L and gDRVI01-H2+VRC01L showing an excellent binding capacity to CN54 GP140 (FIGS. 4C and 4D) and a broad neutralizing breadth (Tables 2A and 2B) were identified. *Escherichia coli* strain carrying the expression vector (gDRVI01-H1) containing the heavy chain gene encoding heavy chain variable region gDRVI01-H1 was deposited at CGMCC under the accession number of CGMCC No. 11883. The sequence encoding the heavy chain variable region contained in the expression vector gDRVI01-H1 is SEQ ID NO:3, and the encoded amino acid sequence of the heavy chain variable region is SEQ ID NO:4. *Escherichia coli* strain carrying the expression vector (gDRVI01-H2) containing the heavy chain gene encoding heavy chain variable region gDRVI01-H2 was deposited at CGMCC under the accession number of CGMCC No. 11884. The sequence encoding the heavy chain variable region contained in the expression vector gDRVI01-H2 is SEQ ID NO:5, and the encoded amino acid sequence of the heavy chain variable region is SEQ ID NO:6. Table 1 shows the sequences and CDRs of heavy chain variable regions gDRVI01-H1 and gDRVI01-H2.

Although the invention has been described with reference to particular embodiments, it is to be understood that these embodiments are merely illustrative of the application of the principles of the invention. Numerous modifications made be made therein without departing from the spirit and scope of the invention.

REFERENCES

1. Dennis R. Burton, Jayashree Pyati, Raju Koduri, Stephen J. Sharp, George B. Thornton, Paul W H. 1. Parren, Lynette S. W Sawyer, R. Michael Hendry, Nancy Dunlop, Peter L. Nara, Michael Lamacchia, Eileen Garratty, E. Richard Stiehm, Yvonne J. Bryson, Yunzhen Cao, John P. Moore, David D. Ho, Carlos F. Barbas III. Efficient neutralization of primary isolates of HIV-1 by a recombinant human monoclonal antibody. *Science.* 1994. 266: 1024-1027.

2. Xueling Wu, Zhi-Yong Yang, Yuxing Li, Carl-Magnus Hogerkorp, William R. Schief, Michael S. Seaman, Tongqing Zhou, Stephen D. Schmidt, Lan Wu, Ling Xu, Nancy S. Longo, Krisha McKee, Sijy O'Dell, Mark K. Louder, Diane L. Wycuff, Yu Feng, Martha Nason, Nicole Doria-Rose, Mark Connors, Peter D. Kwong, Mario Roederer, Richard T. Wyatt, Gary J. Nabel, John R. Mascola. Rational design of envelope identifies broadly neutralizing human monoclonal antibodies to HIV-1. *Science*. 2010. 329:856-861.
3. Jason S. McLellan, Marie Pancera, Chris Carrico, Jason Gorman, Jean-Philippe Julien, Reza Khayat, Robert Louder, Robert Pejchal, Mallika Sastry, Kaifan Dai, Sijy O'Delll, Nikita Patel, Syed Shahzad-ul-Hussan, Yongping Yang, Baoshan Zhang, Tongqing Zhou, Jiang Zhu, Jeffrey C. Boyington, Gwo-Yu Chuang, Devan Diwanji, Ivelin Georgiev, Young Do Kwon, Doyung Lee, Mark K. Louder, Stephanie Moquin, Stephen D. Schmidt, Zhi-Yong Yang, Mattia Bonsignori, John A. Crump, Saidi H. Kapiga, Noel E. Sam, Barton F. Haynes, Dennis R. Burton, Wayne C. Koff, Laura M. Walker, Sanjay Phogat, Richard Wyatt, Jared Orwenyo, Lai-Xi Wang, James Arthos, Carole A. Bewley, John R. Mascola, Gary J. Nabel, William R. Schief, Andrew B. Ward, Ian A. Wilson, and Peter D. Kwong. Structure of HIV-1 gp120 V1/V2 domain with broadly neutralizing antibody PG9. *Nature*. 2011. 480:336-343.
4. Jean-Philippe Julien, Devin Sok, Reza Khayat, Jeong Hyun Lee, Katie J. Doores, Laura M. Walker, Alejandra Ramos, Devan C. Diwanji, Robert Pejchal, Albert Cupo, Umesh Katpally, Rafael S. Depetris, Robyn L. Stanfield, Ryan McBride, Andre J. Marozsan, James C. Paulson, Rogier W Sanders, John P. Moore, Dennis R. Burton, Pascal Poignard, Andrew B. Ward, Ian A. Wilson. Broadly Neutralizing Antibody PGT121 Allosterically Modulates CD4 Binding via Recognition of the HIV-1 gp120 V3 Base and Multiple Surrounding Glycans. *PLoS Pathog*. 2013. 9: e1003342.
5. Jinghe Huang, Gilad Ofek, Leo Laub, Mark K. Louder, Nicole A. Doria-Rose, Nancy S. Longo, Hiromi Imamichi, Robert T. Bailer, Bimal Chakrabarti, Shailendra K. Sharma, S. Munir Alam, TaoWang, Yongping Yang, Baoshan Zhang, Stephen A. Migueles, Richard Wyatt, Barton F. Haynes, Peter D. Kwong, John R. Mascola, Mark Connors. Broad and potent neutralization of HIV-1 by a gp41-specific human antibody. *Nature*. 2012. 491: 406-412.
6. Jinghe Huang, Byong H. Kang, Marie Pancera, Jeong Hyun Lee, Tommy Tong, Yu Feng, Ivelin S. Georgiev, Gwo-Yu Chuang, Aliaksandr Druz, Nicole A. Doria-Rose, Leo Laub, Kwinten Sliepen, Marit J. van Gils, Alba Torrents de la Peña, Ronald Derking, Per-Johan Klasse, Stephen A. Migueles, Robert T. Bailer, Munir Alam, Pavel Pugach, Barton F. Haynes, Richard T. Wyatt, Rogier W Sanders, James M. Binley, Andrew B. Ward, John R. Mascola, Peter D. Kwong, Mark Connors. Broad and potent HIV-1 neutralization by a human antibody that binds the gp41-120 interface. *Nature*. 2014. 515:138-142.
7. Ming Li, Feng Gao, John R. Mascola, Leonidas Stamatatos, Victoria R. Polonis, Marguerite Koutsoukos, Gerald Voss, Paul Goepfert, Peter Gilbert, Kelli M. Greene, Miroslawa Bilska, Denise L. Kothe, Jesus F. Salazar-Gonzalez, Xiping Wei, Julie M. Decker, Beatrice H. Hahn, David C. Montefiori. Human Immunodeficiency Virus Type 1 env Clones from Acute and Early Subtype B Infections for Standardized Assessments of Vaccine-Elicited Neutralizing Antibodies. *J Virol*. 2005. 79:10108-10125.

The invention claimed is:

1. An isolated human monoclonal antibody, or a functional antibody fragment thereof, wherein the antibody comprises a heavy chain variable domain and a light chain variable domain, wherein the heavy chain variable domain comprises:
   (i) VHCDR1, VHCDR2, and VHCDR3 respectively corresponding to VHCDR1, VHCDR2, and VHCDR3 contained in the amino acid sequence of SEQ ID NO:2,
   (ii) VHCDR1, VHCDR2, and VHCDR3 respectively corresponding to VHCDR1, VHCDR2, and VHCDR3 contained in the amino acid sequence of SEQ ID NO:4, or
   (iii) VHCDR1, VHCDR2, and VHCDR3 respectively corresponding to VHCDR1, VHCDR2, and VHCDR3 contained in the amino acid sequence of SEQ ID NO:6, and
   wherein the light chain variable domain comprises VLCDR1, VLCDR2, and VLCDR3 respectively corresponding to VLCDR1, VLCDR2, and VLCDR3 contained in the amino acid sequence of SEQ ID NO:10, and further wherein the antibody is a neutralizing antibody which specifically binds to gp120 of HIV-1.

2. The antibody or antibody fragment of claim 1, wherein the heavy chain variable domain comprises:
   (i) VHCDR1, VHCDR2, and VHCDR3 respectively corresponding to amino acids 31-35, 50-66, and 99-109 of SEQ ID NO:2,
   (ii) VHCDR1, VHCDR2, and VHCDR3 respectively corresponding to amino acids 31-35, 50-66, and 99-109 of SEQ ID NO:4, or
   (iii) VHCDR1, VHCDR2, and VHCDR3 respectively corresponding to amino acids 31-35, 50-66, and 99-109 of SEQ ID NO:6.

3. The antibody or antibody fragment of claim 1, wherein the heavy chain variable domain comprises:
   (i) an amino acid sequence that is at least 85% identical to one of SEQ ID NOs: 2, 4, and 6; and
   (ii) heavy chain VHCDR1, VHCDR2, and VHCDR3 selected from the group consisting of VHCDR1, VHCDR2, and VHCDR3, respectively, of SEQ ID NO:2; VHCDR1, VHCDR2, and VHCDR3, respectively, of SEQ ID NO:4; or VHCDR1, VHCDR2, and VHCDR3, respectively, of SEQ ID NO:6,
   and further wherein the antibody specifically binds to gp120 of HIV-1.

4. The antibody or antibody fragment of claim 1, wherein the light chain variable domain comprises VLCDR1, VLCDR2, and VLCDR3 respectively corresponding to amino acids 24-32, 48-54, and 87-91 of SEQ ID NO: 10.

5. The antibody or antibody fragment of claim 1, wherein the light chain variable domain comprises:
   (i) an amino acid sequence that is at least 85% identical to SEQ ID NO:10; and
   (ii) light chain VLCDR1, VLCDR2, and VLCDR3, respectively, of SEQ ID NO:10, and further wherein the antibody specifically binds to gp120 of HIV-1.

6. The antibody or antibody fragment of claim 1, wherein the antibody is an IgG, IgM, or IgA.

7. The antibody or antibody fragment of claim 1, wherein the antibody fragment is selected from the group consisting of a Fab fragment, a Fab' fragment, a F(ab)'2 fragment, a single chain Fv protein (scFv), and a disulfide stabilized Fv protein (dsFv).

8. A pharmaceutical composition comprising the antibody or antibody fragment of claim 1 and a pharmaceutically acceptable carrier.

9. A method of suppressing or treating HIV-1 infection in a human subject, comprising administering to the human subject an effective amount of the pharmaceutical composition of claim 8.

10. The method of claim 9, wherein the subject has acquired immune deficiency syndrome (AIDS).

11. The method of claim 9, further comprising administering to the subject an anti-viral agent against HIV-1.

12. The antibody or antibody fragment of claim 3, wherein the heavy chain variable domain comprises an amino acid sequence that is at least 90% identical to one of SEQ ID NOs: 2, 4, and 6.

13. The antibody or antibody fragment of claim 3, wherein the heavy chain variable domain comprises an amino acid sequence that is at least 95% identical to one of SEQ ID NOs: 2, 4, and 6.

14. The antibody or antibody fragment of claim 3, wherein the heavy chain variable domain comprises an amino acid sequence of SEQ ID NOs: 2, 4, or 6.

15. The antibody or antibody fragment of claim 5, wherein the light chain variable domain comprises an amino acid sequence that is at least 90% identical to SEQ ID NO: 10.

16. The antibody or antibody fragment of claim 5, wherein the light chain variable domain comprises an amino acid sequence that is at least 95% identical to SEQ ID NO: 10.

17. The antibody or antibody fragment of claim 5, wherein the light chain variable domain comprises an amino acid sequence of SEQ ID NO: 10.

18. The antibody or antibody fragment of claim 1, wherein:
 (a) the heavy chain variable domain comprises:
  (i) an amino acid sequence that is at least 85% identical to one of SEQ ID NOs: 2, 4, and 6; and
  (ii) heavy chain VHCDR1, VHCDR2, and VHCDR3 selected from the group consisting of VHCDR1, VHCDR2, and VHCDR3, respectively, of SEQ ID NO: 2; VHCDR1, VHCDR2, and VHCDR3, respectively, of SEQ ID NO: 4; or VHCDR1, VHCDR2, and VHCDR3, respectively, of SEQ ID NO: 6;
 (b) the light chain variable domain comprises:
  (i) an amino acid sequence that is at least 85% identical to SEQ ID NO: 10; and
  (ii) light chain VLCDR1, VLCDR2, and VLCDR3, respectively, of SEQ ID NO: 10; and
 (c) the antibody or antibody fragment specifically binds to gp120 of HIV-1.

19. The antibody or antibody fragment of claim 1, wherein:
 (a) the heavy chain variable domain comprises an amino acid sequence of SEQ ID NOs: 2, 4, or 6;
 (b) the light chain variable domain comprises an amino acid sequence of SEQ ID NO: 10; and
 (c) the antibody or antibody fragment specifically binds to gp120 of HIV-1.

* * * * *